(12) United States Patent
He

(10) Patent No.: US 10,481,149 B2
(45) Date of Patent: *Nov. 19, 2019

(54) METHOD FOR MEASURING BILE SALT EXPORT TRANSPORT AND/OR FORMATION ACTIVITY

(71) Applicant: Biotranex, LLC, Monmouth Junction, NJ (US)

(72) Inventor: Kan He, Princeton, NJ (US)

(73) Assignee: Biotranex, LLC, Monmouth Junction, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/675,388

(22) Filed: Aug. 11, 2017

(65) Prior Publication Data

US 2017/0343535 A1    Nov. 30, 2017

Related U.S. Application Data

(63) Continuation of application No. 14/781,520, filed as application No. PCT/US2014/041136 on Jun. 5, 2014, now Pat. No. 9,772,325.

(60) Provisional application No. 61/834,944, filed on Jun. 14, 2013.

(51) Int. Cl.
| | |
|---|---|
| *G01N 33/50* | (2006.01) |
| *G01N 33/60* | (2006.01) |
| *G01N 33/92* | (2006.01) |
| G01N 33/58 | (2006.01) |
| G01N 33/68 | (2006.01) |

(52) U.S. Cl.
CPC ......... *G01N 33/5067* (2013.01); *G01N 33/60* (2013.01); *G01N 33/92* (2013.01); *G01N 33/582* (2013.01); *G01N 33/6848* (2013.01); *G01N 2500/00* (2013.01); *G01N 2800/085* (2013.01)

(58) Field of Classification Search
CPC .................................................. G01N 33/5067
See application file for complete search history.

(56) References Cited

U.S. PATENT DOCUMENTS

| | | |
|---|---|---|
| 5,869,265 A | 2/1999 | Dawson |
| 6,780,580 B2 | 8/2004 | LeCluyse et al. |
| 7,229,825 B2 | 6/2007 | Cui et al. |
| 7,601,494 B2 | 10/2009 | Tian et al. |
| 7,604,934 B2 | 10/2009 | LeCluyse et al. |
| 7,682,781 B2 | 3/2010 | LeCluyse et al. |
| 8,129,197 B2 | 3/2012 | Bathori et al. |
| 2005/0003538 A1 | 1/2005 | Cui et al. |
| 2005/0048464 A1 | 3/2005 | Tian et al. |
| 2006/0258000 A1 | 11/2006 | Allen et al. |
| 2007/0250270 A1 | 10/2007 | Vaisberg et al. |
| 2007/0287167 A1 | 12/2007 | Theis et al. |
| 2009/0325297 A1 | 12/2009 | Tian et al. |
| 2010/0035293 A1 | 2/2010 | Brouwer et al. |
| 2010/0173333 A1 | 7/2010 | LeCluyse et al. |
| 2010/0233808 A1 | 11/2010 | Reid et al. |
| 2013/0116218 A1 | 5/2013 | Kaplan et al. |
| 2016/0054305 A1 | 2/2016 | He |

FOREIGN PATENT DOCUMENTS

| | | |
|---|---|---|
| EP | 1163517 B1 | 4/2006 |
| EP | 1659403 B1 | 7/2009 |
| EP | 2292738 A1 | 3/2011 |
| EP | 2112511 B1 | 1/2012 |
| JP | 2010261871 A | 11/2010 |
| JP | 2013017411 A | 1/2013 |
| WO | 2005100545 A1 | 10/2005 |
| WO | 2007132279 A2 | 11/2007 |
| WO | 2007146203 A1 | 12/2007 |
| WO | 2007103406 A2 | 2/2008 |
| WO | 2008022956 A1 | 2/2008 |
| WO | 2007103531 A2 | 10/2008 |
| WO | 2009013254 A1 | 1/2009 |

OTHER PUBLICATIONS

Mita, S et al. "Inhibition of Bile Acid Transport across Na+/Taurocholate Cotransporting Polypeptide (SLC10A1) and Bile Salt Export Pump (ABCB11)-Coexpressing LLC-PK1 Cells by Cholestasis-Inducing Drugs" Drug Metab. Dispos. 2006, vol. 34, No. 9, pp. 1575-1581.

Einarsson, C et al. "Bile Acid Formation in Primary Hepatocytes" World J. Gastroentero. 2000, vol. 6, No. 4, pp. 522-525.

Chiang, Jyl "Bile Acids: Regulation of Synthesis" J. Lipid Res. 2009, vol. 50, pp. 1955-1966.

Jani, M et al. "Kinetic Characterization of Sulfasalazine Transport by Human ATP-Binding Cassette G2" Biol. Pharm. Bull. 2009, vol. 32, No. 3, pp. 497-499.

Kis, E et al. "Mouse Bsep ATPase Assay: a Nonradioactive Tool for Assessment of the Cholestatic Potential of Drugs" J. Biomol. Screen. 2009, vol. 14, No. 1, pp. 10-15 (Abstract).

Kis, E et al. "Effect of Membrane Cholesterol on BSEP/Bsep Activity: Species Specificity Studies for Substrates and Inhibitors" Drug Metab. and Dispos. 2009, vol. 37, No. 9, pp. 1878-1886.

Saito, H et al. "Technical Pitfalls and Improvements for High-speed Screening and QSAR Analysis to Predict Inhibitors of the Human Bile Salt Export Pump (ABCB11/BSEP)" The AAPS Journal 2009, vol. 11, No. 3, pp. 581-589.

(Continued)

*Primary Examiner* — Bin Shen
(74) *Attorney, Agent, or Firm* — Thomas F Woolf; Maria Luisa Palmese; Wuersch & Gering LLP

(57) ABSTRACT

A method is provided to measure modulation of bile salt export transport and/or formation activity in hepatocyte or stable cell line preparations by test agents including but not limited to drugs, drug candidates, biologicals, food components, herb or plant components, proteins, peptides, DNA, RNA. Furthermore, the method is to determine modulation of bile salt export transport and/or formation activity not only by said test agents, but further their metabolites or biotransformed products formed in situ. The bile salt export transport and/or formation activity modulation includes but not limited to inhibition, induction, activation and/or regulation. The method can be practiced to identify test agents, which have potential to cause liver injury, drug-drug interactions, and/or can be used as therapeutic agents for the treatment of cholestasis, abnormality of bile salt metabolism, liver diseases and cholesterol abnormality.

17 Claims, 6 Drawing Sheets

(56) References Cited

OTHER PUBLICATIONS

Ansede, JH et al. "An In Vitro Assay to Assess Transporter-Based Cholestatic Hepatotoxicity Using Sandwich-Cultured Rat Hepatocytes" Drug Metab. Dispos. 2010, vol. 38, No. 2, pp. 270-280.
Morgan, RE et al. "Interference with Bile Salt Export Pump Function is a Susceptibility Factor for Human Liver Injury in Drug Development" Toxicological Sciences 2010, vol. 118, No. 2, pp. 485-500.
Steiner, C et al. "Quantification of the 15 Major Human Bile Acids and Their Precursor 7Alpha-Hydroxy-4-Cholesten-3-One in Serum by Liquid Chromatography-Tandem Mass Spectrometry" J. Chromatography B 2010, vol. 878, pp. 2870-2880.
Wolf, KK et al. "Use of Cassette Dosing in Sandwich-Cultured Rat and Human Hepatocytes to Identify Drugs that Inhibit Bile Acid Transport" Toxicol. In Vitro 2010, vol. 24, No. 1, pp. 297-309.
Padda, MS et al. "Drug Induced Cholestasis" Hepatology 2011, vol. 53, No. 4, pp. 1377-1387.
Dawson, S et al. "In Vitro Inhibition of the Bile Salt Export Pump Correlates with Risk of Cholestatic Drug-Induced Liver Injury in Humans" Drug Metab. Dispos. 2012, vol. 40, No. 1, pp. 130-138.
Kis, E et al. "BSEP Inhibition: In Vitro Screens to Assess Cholestatic Potential of Drugs" Toxicol. In Vitro 2012, vol. 26, No. 8, pp. 1294-1299.
Ellinger, P et al. "Detergent Screening and Purification of the Human Liver ABC Transporters BSEP (ABCB11) and MDR3 (ABCB4) Expressed in the Yeast *Pichia pastoris*" Apr. 4, 2013, PLOS ONE 8(4): e60620. doi:10.1371/journal.pone.0060620.
Hillgren, KM et al. "Emerging Transporters of Clinical Importance: An Update From the International Transporter Consortium" Clin. Pharmacol. Ther. Apr. 8, 2013, doi: 10.1038/clpt.2013.74. [Epub ahead of print].
Pedersen, JM et al. "Early Identification of Clinically Relevant Drug Interactions With the Human Bile Salt Export Pump (BSEP/ABCB11)" Toxicological Sciences 2013, vol. 136, No. 2, pp. 328-343 (Advance Access publication Sep. 6, 2013).
FDA Center for Drug Evaluation and Research Guidance for Industry Drug—Induced live Injury: Premarketing Clinical Evaluation (Jul. 2009). Retrieved Jun. 19, 2015 from the internet: <URL: http://www.fda.gov/downloads/Drugs/.../Guidances/UCM174090.pdf>.
Rose, KA et al. "Hepatobiliary Disposition in Primary Cultures of Dog and Monkey Hepatocytes" Molecular Pharmaceutics 2006, vol. 3, No. 3, pp. 266-274.
Bow, DA et al. "Localization of P-gp (Abcb1) and Mrp2 (Abcc2) in freshly isolated rat hepatocytes" Drug Metab. Dispos. 2008, vol. 36, No. 1, pp. 198-202.
Wakabayashi, Y et al. "Intracellular Trafficking of Bile Salt Export Pump (ABCB11) in Polarized Hepatic Cells: Constitutive Cycling Between the Canalicular Membrane and rab11-Positive Endosomes" Mol. Biol. Cell 2004, vol. 15, pp. 3485-3496.
Hirano, M et al. "Bile Salt Export Pump (BSEP/ABCB11) can Transport a Nonbile Acid Substrate, Pravastatin" J. Pharm. Exp. Ther. 2005, vol. 314, No. 2, pp. 876-882.
Kostrubsky, SE et al. "Inhibition of Hepatobiliary Transport as a Predictive Method for Clinical Hepatotoxicity of Nefazodone" Toxicol. Sci. 2006, vol. 90, No. 2, pp. 451-459.
Fukuda, H et al., "More Relevant Prediction for In Vivo Drug Interaction of Candesartan Cilexetil on Hepatic Bile Acid Transporter BSEP Using Sandwich-cultured Hepatocytes" Drug Metab. Pharmacokinet. 2014, vol. 29, No. 1. pp. 94-96.
Li, N et al., "LC-MS/MS Mediated Absolute Quantification and Comparison of Bile Salt Export Pump and Breast Cancer Resistance Protein in Livers and Hepatocytes across Species" Anal. Chem. 2009, vol. 81, pp. 2251-2259.
Trauner, M et al., "Bile Salt Transporters: Molecular Characterization, Function, and Regulation" Physiol. Rev. 2003, vol. 83, pp. 633-671.
Kostrubsky, VE et al. "Evaluation of Hepatotoxic Potential of Drugs by Inhibition of Bile-Acid Transport in Cultured Primary Human Hepatocytes and Intact Rats" Toxicological Sciences 2003, vol. 76, pp. 220-228.
Funk, C et al. "Cholestatic Potential of Troglitazone as a Possible Factor Contributing to Troglitazone-Induced Hepatotoxicity: In Vivo and In Vitro Interaction at the Canalicular Bile Salt Export Pump (Bsep) in the Rat" Mol. Pharm. 2001,vol. 59, No. 3, pp. 627-635.
Cheng Y et al. "In vitro model systems to investigate bile salt export pump (BSEP) activity and drug interactions: A review" Chem Biol Interact. Dec. 10, 2015. pii: S0009-2797(15)30131-9. doi: 10.1016/j.cbi.2015.11.029. [Epub ahead of print] PubMed PMID: 26683212.; [Update].
Zhang, J et al. "Inhibition of Bile Salt Transport by Drugs Associated with Liver Injury in Primary Hepatocytes from Human, Monkey, Dog, Rat, and Mouse" Chem Biol Interact. Mar. 18, 2016.
Rembacz KP et al. "Unconjugated Bile Salts Shuttle Though Hepatocyte Peroxisomes for Taurine Conjugation" Hepatology 2010, vol. 52, p. 2167-2176.

METHOD FOR MEASURING BILE SALT EXPORT TRANSPORT AND/OR FORMATION ACTIVITY

CROSS REFERENCE TO RELATED APPLICATIONS

This application is a continuation of U.S. National Stage application Ser. No. 14/781,520 filed on Sep. 30, 2015 under 35 U.S.C. § 371 of PCT/US2014/041136, filed on Jun. 5, 2014, which claims priority from U.S. Provisional application No. 61/834,944, filed on Jun. 13, 2013.

TECHNICAL FIELD

The subject matter disclosed herein introduces a novel method to measure the modulation, by test agents on hepatic bile salt export transport and/or formation activity, in incubations of hepatocyte preparations derived from human and animal livers or stable cell lines including but not limited to HepG2 (hepatocellular carcinoma) with bile salt precursor compounds and determining the post-incubation extracellular and/or intracellular bile salt concentrations. Test agents include but are not limited to drugs, drug candidates, biologicals, food components, peptides, proteins, oligonucleotides, DNA, and RNA. Bile salt precursor compounds, also known as bile acids, used in this invention include cholic acid, chenodeoxycholic acid, deoxycholic acid, lithocholic acid, and derivatives thereof incubated separately or in any combination. Bile salts, also known as conjugated bile acids, measured in the invention include glycocholic acid, taurocholic acid, glycodeoxycholic acid, taurodeoxycholic acid, glycochenodeoxycholic acid, taurochenodeoxycholic acid, glycolithocholic acid, and taurolithocholic acid, which can be measured separately or in any combination. Furthermore, this disclosed subject matter relates to applications of said method for measuring test agent modulation of bile salt export transport and/or formation activity in screening paradigms for purposes of assessing potential treatments for hepatic cholestasis, drug-drug interactions, and drug-induced liver injury. A kit to facilitate screening test agents on modulation of bile salt export transport and/or formation is provided.

BACKGROUND ART

Bile Salts: The production of bile is an important function of human and animal liver hepatocytes and plays a crucial role in hepatobiliary and intestinal homeostasis and digestion. [de Buy Wenniger, Bile salts and cholestasis. Digest Liver Diseases 42(6), 409-18, 2010] Bile comprises a highly concentrated solution of bile salts—also known as conjugated bile acids—biliary lipids (phospholipids and cholesterol) and electrolytes. [Kis et al., Effect of membrane cholesterol on BSEP/Bsep activity: specificity studies for substrates and inhibitors, Drug Metabolism and Disposition 37, 1878-1886, 2009] Bile salts are synthesized in the liver via a series of metabolic steps starting from cholesterol. Bile salts and acids are secreted into bile and stored in the gallbladder for release. [Einarsson et al., Bile acid formation in primary human hepatocytes, World journal of Gastroenterology 6(4), 522-525, 2000; Jansen and Faber, 2.3.6 Metabolism of bile acids in Hepatology—From Basic Science to Clinical Practice, Third edition, 2007, 174-181]

Bile salts or conjugated bile acids include glycocholic acid, taurocholic acid, glycodeoxycholic acid, glycochenodeoxycholic acid, taurodeoxycholic acid, taurochenodeoxycholic acid, glycolithocholic acid and taurolithocholic acid (see FIG. 1).

After a meal, the gallbladder contracts, and stored bile is secreted into the intestinal tract where it plays a key role in the absorption of dietary lipids, fat-soluble vitamins, nutrients, and some drugs and drug candidates. In the intestine, approximately 90-95% of secreted bile salts are reabsorbed and returned to the liver and taken up there by hepatocytes—a process called enterohepatic circulation. [Jansen and Faber id. page 174] Enterohepatic circulation serves an important physiological function not only for the recycling of bile salts and absorption of dietary lipids, fat-soluble vitamins, nutrients and some drugs and drug candidates, but also for the regulation of whole-body lipid metabolism. [Chiang, Bile acids: regulation of synthesis. Journal of Lipid Research 50, 1955-1966, 2009]

Bile salts are indispensable for the formation of bile flow; secretion of cholesterol and phospholipids from the liver, formation of mixed micelles that keep fat-soluble organic compounds in solution in the gut, promotion of the dissolution and hydrolysis of triglycerides by pancreatic enzymes, and act as signaling molecules in the regulation of enzymes and transporters of drugs and intermediary metabolism. [Jansen and Faber, id. page 178]

Biosynthesis of bile salts involves a multi-step process beginning with the initial oxidation of cholesterol by cytochrome P450 oxidase enzymes (also known as mixed function oxidases) present in human hepatocytes, (FIG. 2) [id. page 174, Chiang id. page 1955] Two main routes exist for the conversion of cholesterol to the primary bile acids cholic acid (CA) and chenodeoxycholic acid (CDCA):] a classic or neutral pathway involving initial oxidation by the cytochrome P450 CYP7A1 (cholesterol 7α-hydroxylase) and alternative or acidic pathway involving side chain hydroxylation with cytochrome P450 CYP27A1 (sterol 27-hydroxylase). [Jansen and Faber id. page 174] CYP7A1 is regarded as the rate-limiting enzyme in bile acid synthesis and deficiencies in animal models have been associated with severe liver failure. [Jansen and Faber id.] The CYP27A1 product is not a substrate fur CYP7A1 but instead is oxidized by another cytochrome P450 enzyme named CYP7B1. From there, the neutral and acidic pathways overlap producing CDCA and CA. Other minor oxidative pathways may also contribute to bile acid synthesis. [Jansen and Faber id.] Most bile acids, including CA and CDCA, are conjugated to the amino acids glycine (G) and taurine (T) by two enzymes: bile acid:CoA synthase (BACS) and bile acid: amino acid transferase (BAT). [Chiang id. page 1957] These glycine and taurine bile acid conjugates act to decrease the toxicity and increase the aqueous solubility of unconjugated bile acids for secretion into bile. [Chiang id. page 1957] In the intestine, the glycine- and taurine-conjugated CA and CDCA can be deconjugated releasing CA and CDCA, which can be acted on by gut bacterial 7α-dehydroxylase to remove their 7α-hydroxy groups and thereby produce the secondary bile acids deoxycholic acid (DCA; 3α-12-dihydroxy CA) and lithocholic acid (LCA; 3α-monohydroxy). [Chiang id.] CA, CDCA, and DCA can be reabsorbed in the intestine and transported back to the liver to inhibit bile acid synthesis. Most of LCA is excreted in feces. The reabsorbed bile acids are further conjugated to amino acids producing the bile salts of CA, CDCA, and DCA.

Amino acid conjugated bile acids are termed conjugated bile acids or bile salts while non-amino acid conjugated bile acids are termed free. Bile acids and salts can be potentially toxic to cells and their concentrations under physiological conditions are tightly regulated. As mentioned above, bile acids are important and potent signaling molecules in the liver and intestine. Both free and conjugated bile acids bind to the ligand-binding domain of the nuclear transcription factor farnesoid X receptor (FXR; NR1H4), regulating FXR and associated gene transcription product FGF19 and ultimately regulating bile acid synthesis, excretion, and transport. [Chiang id. page 1956] Additionally, free and conjugated bile acids have been found to bind and activate pregnane X receptor (PXR; NR1I2) and vitamin D receptor (VDR; NR1I1). [Chiang id.]

The process of producing bile salts essentially results in the conversion of the hydrophobic cholesterol molecule into an amphipathic molecule that can serve physiologically as a detergent for absorption and transport of nutrients, fat-soluble vitamins, drugs, and other chemicals.

Bile salts have important acid-base properties, especially in the intestinal duodenum where pH values range from 3 to 5 units. [Costanzo, Physiology, $4^{th}$ edition, Saunders Elsevier, Philadelphia, Pa., 2010] Unconjugated bile acids have pKa values ranging near 7 pH units. In the duodenum, unconjugated bile acids are almost exclusively in the unionized protonated form and therefore are relatively insoluble in water and readily reabsorbed by the intestinal epithelium cells. Bile salts or conjugated bile acids have much lower pKa values ranging from 1 to 4 units whereas the conjugated bile salts are ionized or deprotonated in the duodenum, are more water soluble, and are more able to emulsify lipids and other non-water-soluble agents.

Bile salts or conjugated bile acids in the duodenum having been ionized, are not readily reabsorbed and can build up in concentrations to allow for formation of micelles and solubilized lipids which play significant roles in processes such as elimination of cholesterol from the body, removal of catabolites produced by the liver, and emulsifying lipids, fat-soluble vitamins, and some drugs and drug candidates. [Jansen and Faber id. page 178]

Hepatocytes: Hepatic parenchymal cells, or hepatocytes, are polyhedral or spherical in nature and account for approximately 60% of the cells in the liver; they represent 80% or more of the total liver volume. [de la Iglesia, Morphofunctional aspects of hepatic structure, Handbook of Drug Metabolism, edited by T. F. Woolf, 1999, page 83] Hepatocytes are polar in nature and one skilled in the art would recognize what is termed an apical (canalicular) membrane or domain and a basolateral (blood or sinusoidal domain) membrane or domain. The hepatocyte basolateral membrane or domain is involved in the uptake of drugs and xenobiotics into the cell, while the apical membrane or domain provides a route for intracellular produced bile salts to be excreted or transported into bile flow and eventually to the common bile duct for secretion into the intestine.

Hepatocytes have specialized transport systems or transcellular transporters located at the basolateral membrane and the apical membrane. [Morgan et al., Interference with bile salt export pump function is a susceptibility factor for human liver injury in drug development, Toxicological Sciences 118(2), 485-500, 2010] These hepatobiliary transporters maintain liver homeostasis by regulating intracellular exposure to endobiotic and xenobiotic chemicals. Transport systems comprising of specific transporter proteins have been extensively investigated. Transporters at the basolateral membrane are involved in hepatocellular uptake of various substrates from the blood and sinusoids, elimination to the blood and sinusoids, or both depending on the transporter. Transporters on the apical membrane, however, are exclusively efflux transporters, mediating secretion into the bile flow of various substrates including bile acids and salts. [Morgan et al., id. page 485]

Bile Salts Export Pump: BSEP (all capitalized letters reflect human transporter gene product) is a membrane-associated transporter protein located on the hepatocyte apical or canalicular membrane and is a member of the superfamily of ATP-binding cassette (ABC) transporter proteins, which are responsible for the extracellular transport or secretion of conjugated and unconjugated bile acids and salts into the bile canaliculi. [Kis et al., BSEP inhibition: in vitro screens to assess cholestatic potential of drugs, Toxicology In Vitro 26(8), 1294-9, 2012] BSEP is also known as ATP-binding cassette, sub-family B member 11, ABCB11 which is the protein product of the human ABCB11 gene (italics reflect the human gene). BSEP was first cloned in 1998 from rat and identified as the "sister of P-glycoprotein (sPGP)", based on its close amino acid sequence similarity to P-glycoprotein. [Kis et al., Effect of membrane cholesterol on BSEP/Bsep activity: species specificity studies for substrates and inhibitors, Drug Metabolism and Disposition 37, 1878-1886, 2009, page 1878] BSEP displays higher transport affinity binding for tauro- and glycochenodeoxycholic acid and lower for taurocholic acid glycocholic acid and tauroursodeoxycholic acid. [Jansen and Faber id. page 178] BSEP can transport to a limited extent unconjugated bile acids. [id.] BSEP, in addition to exporting bile salts, can also export some xenobiotics and drugs including pravastatin and vinblastine. [Morgan et al., id. page 485]

Rat and mouse orthologs of the human BSEP have similar amino acid sequences sharing 82% and 80%, respectively. [Yabutichi H, et al, Cloning of the dog bile salt export pump (BSEP; ABCB11) and functional comparison with the human and rat proteins, Biopharmaceutical Drug Disposition, 29(8), 441-8, 2008] BSEP is specialized for transporting monovalent bile salts taurine and glycine conjugates—through the canalicular membrane against a concentration gradient in an ATP-dependent manner. [Kis et al., id. page 1878] BSEP transport of bile salts is a saturable process with $K_m$ values for bile salts in the low micromolar range. [Kis id.] The sensitivity to impairment in BSEP transport function appears to display species specificity. [Kis id.] Mutations in human BSEP can lead to progressive intrahepatic cholestasis and liver failure (see below).

Additional ABC transporters expressed at the apical and basolateral membrane include multidrug-resistance related protein MRP2 (ABCC2), breast cancer resistance protein BCRP (ABCG2, also known as MXR) and multidrug-resistance protein MDR1 (ABCB1, also known as P-glycoprotein). [Chandra and Brouwer, Pharmaceutical Research 21(5) 719-735, 2004]

In humans, the levels of the various transporter proteins are subject to genetic polymorphism in the encoding genes as well as in these transcription factors. Adverse drug reactions may be caused by genetic or disease-induced variations of transporter expression or drug-drug interactions at the level of these transporters. [Faber et al., Drug transport proteins in the liver, Advanced Drug Delivery Reviews 55(1), 107-24, 2003]

Drug-Induced Liver Injury (DILI): Drug-induced liver injury encompasses a spectrum of clinical diseases ranging from mild biochemical abnormalities to acute liver failure. [Hussanin and Farrington, Idiosyncratic drug-induced liver injury; an overview, Expert Opinion in Drug Safety 6(6), 673-84, 2007] Most frequently, the underlying mechanism of DILI is poorly understood. In some cases of DILI, the liver injury is categorized as idiosyncratic—unknown etiology. [Wolf et al., Use of cassette dosing in sandwich-cultured rat and human hepatocytes to identify drugs that inhibit bile acid transport, Toxicology In Vitro 24(1), 297-309, 2010; Lee, Drug-induced hepatotoxicity, New England journal of Medicine 349(5), 474-85, 2003] The incidence of DILI induced hepatotoxicity in clinically marketed drugs is relatively rare, ranging from 1 in 5,000 to 1 in 10,000 or less. This is particularly true for DILI that results in severe liver injury leading to irreversible liver failure that can be fatal or require liver transplantation. DILI is a major cause of removal of approved drugs from the United States market resulting in removal of clinically significant therapeutics from patients in need of such therapy. [FDA Guidance for Industry: Drug-induced liver injury—premarketing clinical evaluation, July 2009; Ansede et al., An in vitro assay to assess transporter-based cholestatic hepatotoxicity using sandwich-cultured rat hepatocytes. Drug Metabolism and Disposition 38, 276-280, 2010] Additional consequences of DILI include class action lawsuits against the innovator company (with multi-million of dollar settlements), while adding additional time, expense, and uncertainty to the drug discovery and development process.

Because the modern drug development process requires extensive preclinical testing of drug candidates and subsequent clinical trials, drugs that do ultimately lead to DILI are rare. Drug candidates that display a toxic potential are usually removed from development and never reach the market. [FDA Guidance id.] Nevertheless, drugs that later result in DILI do get approved. Reasons for this may involve the relatively rare nature of the adverse event and that clinical trials are conducted in a closely controlled patient environment with a limited number of subjects for a limited time. Following marketing approval, the number of individuals administered a therapeutic agent will be much greater, periods of treatment may be much longer, and patients are less well monitored. Individuals display a wide variability in hepatic function and can differ greatly with respect to inherent hepatic metabolic function, environmental factors and co-medications. Risk factors for DILI include age, sex and genetic polymorphisms of drug-metabolizing enzymes such as cytochrome P450. In patients with human immunodeficiency virus, the presence of chronic viral hepatitis increases the risk of antiretroviral therapy hepatotoxicity. [Hussaini and Farrington, id. Abstract]

The relatively low incidence rate of DILI creates difficulties in detecting and diagnosing it; both for tests used and for numbers of patients needed. There is no finding that indicates DILI with certainty, including liver biopsy. Because DILI may simulate any known liver disease, the histopathologic picture frequently is reported to be "compatible with" the clinical and laboratory information available, but is not often diagnostic. Therefore, the diagnosis of DILI is one of exclusion, in which sufficient clinical information must be gathered to rule out other possible causes of the abnormal findings. This diagnosis by exclusion requires collecting considerable data at the time of the acute clinical situation, a process that frequently is not well or thoroughly done, so that available information is inadequate to establish the likelihood of drug causality with any reasonable degree of confidence. [FDA Guidance, page 3-7]

In most controlled clinical trials, monitoring is done to detect hepatic injury by serum enzyme (typically amino-transferases) activity increases. Because risks associated with the new drug are unknown, caution has dictated that stopping rules be used to limit liver damage during the trial. For safety reasons, the drug may be stopped before the full implications of its possible toxicity can be determined. Extrapolation of such data, despite early withdrawal of the drug in many cases, is used to predict the likelihood of future severe toxicity when the drug is used clinically.

For interpreting data from patients exposed to drugs in clinical trials, there is a hierarchy of findings that indicate progressively severe liver injury, beginning with serum amino-transferase activities as the most frequently abnormal and most sensitive test. [FDA Guidance id] In many clinical trials of new drugs, up to 15% of study patients (or even more) may demonstrate mild elevations of alanine amino-transferase (ALT) or aspartate aminotransferase (AST) activities. The threshold required to consider either more frequent monitoring of blood levels, or stopping the drug, is variously placed at twice the upper limit of the normal or reference range (2×ULN), 3×ULN, or 5×ULN. Monitoring is typically performed on a monthly basis but may be shortened to biweekly or weekly if elevations in serum enzyme levels are noted. According to the FDA guidance on drug-induced liver injury:

Discontinuation of Treatment Should be Considered

ALT or AST>8×ULN
ALT or AST>5×ULN for more than 2 weeks
ALT or AST>3×ULN and (TBL>2×ULN or INR>1.5)
ALT or AST>3×ULN with the appearance of fatigue, nausea, vomiting, right upper quadrant pain or tenderness, fever, rash, and/or eosinophilia (>5%)
TBL—Total bilirubin Levels
INR—Increase plasma thrombin time
FDA Guidance for Industry—Drug induced liver injury: premarketing clinical evaluation, 2009, page 10

Levels of 10×ULN typically mandate immediate cessation and are considered more serious signals but still do not represent true tests of liver function. Yet great difficulties persist in making accurate attribution of causality as to whether the abnormalities seen are caused by DILI or by some other disorder. [FDA Guidance, pages 3-7, 10]

Even modest increases of serum total bilirubin concentration may represent the beginning of reduced bilirubin excretion capacity, provided Gilbert's syndrome and other unrelated causes of bilirubin elevation could be excluded. It is truly a function of the liver to clear plasma of bilirubin and excrete it into the bile. The late Hyman Zimmerman in 1978 and again in 1999 proposed that appearance of jaundice associated with drug-induced hepatocellular injury indicated possible mortality in 10 to 50% of patients showing that combination of abnormalities, based on his careful review of many clinical trials and literature reports. [FDA Guidance page 4]

Another commonly done test, the blood prothrombin time (or its derivative Internationalized Ratio, INR) may be useful as a liver function test (of protein synthesis). In acute liver failure caused by acetaminophen overdose, increases in INR may precede rises in total bilirubin levels. Thus, only a small decrement in liver function in pre-approval trials may provide a signal that additional and more severe cases may occur when larger numbers of patients are exposed. The full impact of this may not be realized until after approval for clinical use and marketing.

The condition of cholestasis occurs when bile and bile fluids cannot flow from the hepatocytes to the duodenum. The accumulation of bile salts in hepatocytes can lead to cellular apoptosis, necrosis and mitochondrial dysfunction. [Wolf et al., id. page 298] Cholestasis may result from physical obstructions—gallstones or tumors, or from metabolic disorders—drugs interfering with BSEP and other transporters.

BSEP inhibition and DILT: ATP-dependent transporters expressed on the apical plasma membrane domain of hepatocytes are important mediators of canalicular bile flow (see above). [Morgan et al., id. page 485] impaired bile flow arising from genetically determined defects in transporters has been implicated in various inherited forms of cholestatic liver disease in humans. Genetic defects or mutations in BSEP are associated with at least three clinical forms of liver disease: (1) progressive familial intrahepatic cholestasis type 2 (PFIC2); (2) benign recurrent intrahepatic cholestasis type 2 (BRIC2); and (3) intrahepatic cholestasis of pregnancy. [Morgan et al., id. page 486] in the case of PFIC2, the condition has been associated with one or more polymorphisms in the genetic code for BSEP leading to inadequate BSEP function and associated liver injury. PFIC2 is characterized by progressive liver damage usually requiring transplantation while BRIC2 is characterized by intermittent and non-progressive cholestasis.

BSEP protein levels have been correlated with taurocholate transport activity in in vitro studies showing that patients with PFIC2 and BRIC2 gene mutations correlate with decreased protein expression. [Byrne et al., Missense mutations and single nucleotide polymorphisms in ABCB11 impair bile salt export pump processing and function or disrupt pre-messenger RNA splicing, Hepatology 49, 553-567. 2009] Studies indicate that the extent of decrease in BSEP expression and function corresponds to disease outcome. [Morgan et al., id. page 486; Kagawa et al 2008]

Interference in BSEP function can lead to impaired hepatobiliary secretion of bile acids and salts leading to increased serum and tissue levels of bile acids and subsequent cellular mitochondrial damage, apoptosis (programmed cell death) and necrosis. [Maillette de Buy Wenniger, Bile salts and cholestasis, Dig Liver Dis. 42(6) 409-18, 2010 ]

Knockout mice have provided further insight into the complex interrelationships between expression of individual bile salt transporters, bile flow, and liver injury. Homozygous Bsep (mouse bile salt transporter protein) knockout mice were shown to develop severe cholestasis when fed a bile acid-enriched diet, whereas only mild cholestasis was observed when animals were fed a normal diet. This result has been attributed to adaptive changes in expression of other enzymes and transporters Bsep (−/−) mice, which enable them to cope with the lack of functional Bsep expression unless challenged with a high dietary bile acid load. [Wang et al., Sever cholestasis induced by cholic acid feeding in knockout mice of sister of P-glycoprotein, Hepatology 38(6), 1489-99, 2003, Wang et al., Compensatory role of P-glycoproteins in knockout mice lacking the bile salt export pump, Hepatology 50(3), 948-56, 2009] Additional transporters have been implicated in cholestatic liver injury via studies undertaken in knockout mice include Mdr2 (the rodent ortholog of human MDR3). [Fickert et al., Regurgitation of bile acids from leaky bile ducts causes sclerosing cholangitis in Mdr2 (Abcb4) knockout mice, Gastroenterology 127(1), 261-74, 2004]

Therapeutic agents that interfere with BSEP function are often associated with liver liabilities in humans. [Morgan et al., id. page 486] Examples of drugs implicated in human liver injury where BSEP has been an implicated mechanism include bosentan (an endothelia antagonist for pulmonary arterial hypertension [PAH]), erythromycin estolate (a macrolide antibiotic), nefazodone (5-HT$_2$ receptor antagonist for depression), CI-1034 (an experimental endothelin antagonist for pulmonary arterial hypertension [PAH]), and CP-724,714 (an experimental HER2 kinase inhibitor for oncology). [Morgan et al., id. page 486]

Agents that interfere with BSEP function and display liver injury in humans often are not associated with liver injury in preclinical animal investigations indicative of species differences. [Stieger et al., Role of the bile salt export pump, BSEP, in acquired forms of cholestasis, Drug Metabolism and Disposition 42, 437-445, 2009] This discrepancy in predicting liver toxicity of preclinical animal models is a significant concern for the pharmaceutical industry and increases the risk of unexpected liver injury in clinical development.

BSEP Inhibition and Drug-Drug Interactions: The potential for BSEP inhibitors to inhibit drug elimination was investigated in sandwich-cultured rat hepatocytes. [Jemnitz et al., Biliary efflux transporters involved in the clearance of rosuvastatin in sandwich cultured of rat hepatocytes, Toxicology in Vitro 24(2), 605-10, 2010] In this study, the 3-hydroxy-3-methylglutaryl coenzyme A reductase inhibitor rosuvastatin, which is eliminated primarily unchanged by transporters, was used as a marker of transporter elimination. Various known inhibitors of elimination transporters were tested for effect on rosuvastatin elimination including the BSEP inhibitors cyclosporine A, glibenclamide and troglitazone. Results showed that cyclosporine A, glibenclamide and troglitazone interfered 32.6%, 29.3% and 20.6%, respectively, with rosuvastatin elimination. The investigators concluded a potential exists for drug-drug interactions with test agents that interfere with BSEP function.

BSEP Function Assays: In standard in vivo preclinical animal tests of drugs and drug candidates, agents found to interfere with BSEP function often don't induce significant liver injury; but nevertheless, have been associated with significant liver injury when administered to man. [Morgan et al., id. page 486] The inability of animal testing to predict the human hepatotoxicity potential of a drug, drug candidate, biological, food component, chemical, peptide, protein, oligonucleotide, DNA and RNA has led scientists skilled in the art to develop in vitro test model systems for BSEP function. These in vitro model systems include but not limited to:

(1) Sandwich-cultured hepatocyte (SCH) model prepared using primary animal or human hepatocytes;
(2) BSEP transfected Sf9 insect cell membrane vesicle models;
(3) Canalicular membrane vesicles (CMV) derived from rat and human whole liver; and
(4) Doubly-transfected with BSEP and sodium taurocholate co-transporting polypeptide (NTCP).

Sandwich-Cultured Hepatocyte (SCH): Human and rat SCH is an in vitro model system that maintains many in vivo structural and functional characteristics of the hepatocyte, including canalicular and basolateral membrane domains, expression and localization of liver-specific proteins, and functional bile excretion into sealed canalicular networks. [Wolf et al., id. page 298] Human and rat SCH have been used to study the inhibitory effects of drugs including troglitazone, nefazodone, and anti-retroviral agents.

Initial culturing methods employed for SCM led to realization of problems that diminish the ability of in vitro cultures to predict in vivo responses. [US2010035293A1 paragraph 0005] For example, culturing hepatocytes in the sandwich configuration form canalicular network(s) sealed by tight junctions, analogous to closed compartments, into which bile salts, bile acids and other components of bile are excreted. Due to the closed nature of the canalicular compartments, substances excreted from hepatocytes accumulate in these compartments. Over multiple days in culture, this results in cholestatic condition, wherein in bile is trapped in the bile ducts or compartments. Due to the "bask-up" of the trapped bile salts and acids and other endogenous substances the hepatocytes may attempt to compensate by up-regulation or down-regulation of various transport proteins. In addition metabolic pathways also may be affected by the degree of cholestasis, leading to induction or inhibition of various enzymes including drug-metabolizing enzymes. [US2010035293A1 paragraph 0020] In an attempt to address this limitation, a process of pulsing the SCH at various time intervals by exposing the hepatocyte culture to a calcium-free buffer that releases the accumulated bile from the canalicular compartments. [US2010035293A1 paragraph 0021-0022] Such a method could reduce cholestasis in cultured hepatocytes and potentially be used as a model to predict the in vivo metabolism of compounds of interest. [US2010035293 paragraph 007] Further, such a method could allow for the development of models to evaluate the in vivo toxicity and biliary excretion of compounds of interest. [id.] Since SC human hepatocytes also retain metabolic capabilities, this model may allow for investigation of the interplay between many of the processes that take place in vivo. [Ghibellini et al., Methods to evaluate biliary excretion of drugs in human; an update review, Molecular Pharmacology 3(3), 198-211, 2006]

The pulsed SCH method assumes that regularly pulsing the in vitro hepatocyte culture will provide a system that more closely mimics in vivo hepatocytes, thereby providing a system that can not only assess transporter expression and function, but also be of use in evaluating hepatic toxicity and cholestasis. [US2010035293 paragraphs 44-47]

Nevertheless, the pulsed approach involves a complex series of steps involving using freshly isolated rat or human hepatocytes plated on gelled collagen coated 6-well plates and overlaying the cells with a layer of gelled collagen one day after plating to form the sandwich-culture configuration. [US2010035293 paragraph 51] The SCH culture is then pulsed at specific times for specific lengths with Hank's balanced salt solution (HBSS) with calcium (HBSS+Ca) or calcium-free HBSS (HBSS−Ca) followed by removal of the buffer. The frequency and length of pulsing can be important—incubation of HBSS−Ca for 30 minutes once per day or incubation of HBSS−Ca for 15 minutes twice per day. [US2010035293 paragraph 51] Clearly, the system is complex, has been developed with freshly prepared hepatocytes, and requires a high level of expertise to practice, and the requirement for frequent pulsing creates problems for contamination by microbes. The potential for differences in transport function between rat and human SCH in response to pulsing was not addressed. [Wolf et al., id. page 308]

Another issue with the SCH model is the limited number of sample wells available for experiments. In an attempt to address this problem, a modified method using an approach of cassette testing, incubations of multiple test agents in the same sample well, was described. [Wolf et al id.] The use of cassette testing of drug candidates, two to four drug candidates per incubation well, can lead to complex results—false positives and negatives, requiring follow-up testing of individual agents. The method has similar issues as described above along with a requirement for radiolabeled bile acids to measure transport activity. Because of the limited availability of fresh human hepatocytes and potential species differences with rat hepatocytes, the method is limited for any routine test agent-screening paradigm.

BSEP Transfected Sf9 Insect Cell Membrane Vesicles: The Sf9 system is widely used expression system for investigations of plasma membrane proteins properties. Because of its ability to express in significant amounts various membrane proteins, the system has been adapted to use with ABC transporters including human BSEP and various animal species Bsep. [Kis et al., id. page 1879; U.S. Pat No. 8,129,197 column 2 lines 38-45]. Assay systems based on insect cell membrane preparations are generally stable, reliable, easy to handle and several assay formats are offered. [U.S. Pat No. 8,129,197 id.] Nevertheless, insect cell membrane preparation assays differ when compared to mammalian cell based assays, which questions their value as useful and relevant assay systems tear drug development. [U.S. Pat. No. 8,129,197 column 2 lines 46-50] Differences include high basal ATPase activity making transport assays less sensitive. [U.S. Pat. No. 8,129,197 column 2 lines 51-54] Differences between insect and mammalian membrane preparations have been observed in the activity of transporters and their sensitivity for drugs including sulfasalazine, topotecan, prazosin and methotrexate. [U.S. Pat. No. 8,129,197 column 2 lines 63-67] Some of these differences may be due to improper protein glycosylation and low Sf9 membrane cholesterol content. [Kis et al. id. page 1883]

In an attempt to address this issue, Kis et al., added cholesterol to the BSEP/Bsep Sf9 transfected cell cultures to load the prepared membrane vesicles with additional cholesterol. [Kis et al., id. page 1879] The optimized treatment increased the cholesterol 3- to 4-fold compared to untreated membrane vesicles. Inside-out vesicles are incubated at 37° C. for 5 min using 50 μg protein/well in the presence of 4 mM ATP and 2-μM total glycocholate (including $^{14}$C-glycocholate). The reaction is stopped by addition of ice-cold wash buffer with consecutive rapid filtration through Millipore Corporation (Billerica, Mass.) B-glass fiber filters of a 96-well filter plate. After washing five times with 200 μL of ice-cold wash buffer, the filters are dried, and the retained radioactivity measured in scintillation mixture. Species comparison of cholesterol loading showed the most pronounced effect on rat protein, whereas the activity of human BSEP was least affected by the treatment. [Kis et al., id. page 1881] In the assay, troglitazone and glibenclamide, compounds known to be cholestatic humans, displayed species-specific inhibitory profiles. Results show that cholesterol loading makes BSEP/Bsep work more efficiently (higher $V_{max}$), while not apparently changing the affinity ($K_m$) for the transporter for most substrates tested. Nevertheless complexity of preparing the inside-out membrane vesicles and the differences between hepatocyte membranes and insects limits the utility of this method for predicting test agent inhibition potential. In addition, the method has issues of sensitivity, ease of use and requirement of radiolabeled bile salts.

A modified version of this method involving a taurochenodeoxycholate (TCDC) ATPase activity has been designed to be more user friendly, sensitive, and minus the radiolabeled bile salts. [Kis et al., Mouse Bsep ATPase assay: a nonradioactive tool for assessment of the cholestatic potential of drugs, Journal Biomolecular Screen 14(1), 10-15, 2009 (Abstract)] Comparison of TCDC transport measured by a vesicle transport assay and the TCDC-stimulated ATPase assay using cholesterol loaded transfected Sf9 insect inside-out vesicles showed ATPase assay to be sensitive for detection of transport function. A good rank order correlation was found between $IC_{50}$ values measured in TCDC-stimulated mouse Bsep ATPase assay and in the human BSEP vesicular transport assay utilizing taurocholate (TC)

as probe substrate. The method may complement the human BSEP-mediated taurocholate vesicular transport inhibition assay.

Saito et al 2009 describes many issues its preparing Sf9 inverted (inside-out) membrane vesicles including the tinting of harvesting of Sf9 cells after baculovirus infection. [Saito et al., Technical pitfalls and improvements for high-speed screening and QSAR BSEP, The AAPS Journal, 11(3), 581-589, 2009, page 582] The study further highlights the importance of maintaining high integrity of the membrane vesicles used in transport assays.

In summary, the assay suffers from issues of transporter activity in membranes between insect and human/animal hepatocytes, complexity in preparing the transfected insect inside-out vesicles, the use of radiolabeled bile salts, and the inability to assess indirect affects (i.e. metabolism) of test agents on transport. Further, the assay does not allow for measuring formation of bile salts and test agent derived metabolites.

Canalicular Membrane Vesicles (CMV): The CMV has been used a model to study Bsep-mediated interactions isolated from humans and animals because this system contains all the relevant canalicular transporters at an expression level close to physiological. However, species specificity studies using CMVs from humans are difficult because of limited access to human samples and the complexity of dealing with polymorphisms. [Ghibellini et al., id. page 205; Kis et al., id. page 1883; Horikawa et al., Potential cholestatic activity of various therapeutic agents assessed by bile canalicular membrane vesicles isolated from rats and humans, Drug Metabolism and Pharmacokinetics 18, 16-22, 2003] Nevertheless, CMVs prepared from primary hepatocytes have distinct advantages over transfected systems: the native membrane environment is in place during isolation from the other cellular components, and all the hepatic transport systems are present. Membrane vesicles can be prepared, stored frozen, and used as needed; however, isolation of basolateral and canalicular fractions is labor intensive and complete purity is never achieved. [Ghibellini et al. id. page 205]

The CMV method was used to evaluate the potential of 15 therapeutic agents, known to cause cholestasis, to inhibit BSEP transports. The study was conducted using rat CMV. These results suggest that the majority of cholestasis-inducing drugs have a minimal inhibitory effect on rat BSEP and MRP2 although species differences inhibitory potential should be considered, especially in the case of BSEP. [Horikawa et al, id.]

Doubly-Transfected Cell lines: A cell-based assay system in which a liver uptake transporter (human sodium taurocholate co-transporting polypeptide [NTCP]) is constitutively expressed together with a liver export pump (ABC transporter—human BSEP) in the polarized canine kidney cell line MDCKII. [US2007/0287167 paragraph 0007] The resulting dog kidney cell line, therefore, contains human NTCP together with human BSEP. The cells are cultivated in 6-well filter inserts on a porous filter membrane that separates the basolateral membrane domain from the apical membrane domain. Test compounds are added to either the apical domain compartment or basolateral domain compartment for transcellular (vectorial) transport measurements in both directions. Samples are taken from each compartment at designated time periods. Substrates of the combination expressed transporters display significant net transport from basolateral to the apical compartment when compared to un-transfected cell. This method can be used to assess the test compound potential to participate in hepatobiliary elimination. The method can also be used to investigate drug-drug interaction potential between two test compounds. [id., paragraph 0010] Nevertheless, the system differs significantly from that of human hepatocytes.

Rationale for the Invention

A continued need exists for an in vitro method that can more reliably, routinely and accurately be used to study in vivo hepatobiliary processes including bile salt export transport and/or formation activity. The method should be adaptable and scalable to modern drug discovery screening paradigms. The method should be flexible to allow investigation of test agent-derived metabolites on bile salt export transport and/or formation. The presently disclosed subject matter offers the ability to assess test agent effect on bile salt export transport and/or formation. Furthermore the method offers potential to decrease the use of animals in preclinical drug development. Finally, the results from the present method can be used to predict test agent potential fix drug-induced liver injury, cholestasis, drug-drug interactions.

BRIEF DESCRIPTION OF THE INVENTION

A method is presently disclosed to measure modulation of bile salt export transport and/or formation activity in hepatocyte or stable cell line preparations by test agents including but not limited to drugs, drug candidates, biologicals, food components, herb or plant components, proteins, peptides, DNA, RNA. Furthermore, the method is to determine modulation of bile salt export transport and/or formation activity, not only by said drugs, drug candidates, biologicals, food components, herb or plant components, proteins, peptides, oligonucleotides, DNA, and RNA, but further their metabolites or biotransformed products formed in situ. The bile salt export transport and/or formation activity modulation includes but is riot limited to inhibition, induction, activation and/or regulation.

More specifically, an in vitro method is provided using hepatocyte preparations from human and animal livers or stable cell lines such as HepG2 that are incubated with a bile salt precursor compound(s) and a test agent to determine the test agent's effect on inhibition, induction, activation and regulation of bile salt export transport and/or formation. The hepatocyte preparations include suspensions of hepatocyte in an incubation buffer or hepatocytes plated on a suitable medium or support. Stable cells lines such as HepG2 can be suspended in a suitable incubation buffer or plated on a suitable medium or support. The source of hepatocytes can be from freshly prepared human or animal livers or can be cryopreserved hepatocytes prepared from human or animal livers.

The bile salt precursor compounds include but are not limited to cholic acid, chenodeoxycholic acid, deoxycholic acid and lithocholic acid. The bile salt precursor compounds further include all natural bile acids and their derivatives, which can be made by chemical and biological means. The bile salts or conjugated bile acids include but are not limited to glycocholic acid, taurocholic acid, glycodeoxycholic acid, taurodeoxycholic acid, glycolithocholic acid, taurolithocholic acid, glycochenodeoxycholic acid and taurochenodeoxycholic acid. The bile salts or conjugated bile acids include all natural bile salts and their derivatives, which can Le made by chemical and biological means.

Furthermore, the present subject matter describes procedures, incubation conditions and cell culture components to maintain and monitor bile salt export transport and/or formation in hepatocyte preparations, and the means to determine the concentrations of bile salts. These include but are not limited to the concentration of hepatocytes, the incubation time, the concentrations of bile salt precursor compounds, the means to separate extracellular and intracellular portions of bile salts, the procedures to prepare the cells and to perform the incubations. The means to determine the concentrations of bile salts include but are not limited to HPLC, mass spectrometry (MS), liquid chromatography mass spectrometry, radioactive counting, and fluorescence.

Even furthermore, the present subject matter describes a method that can be used with stable cell preparations derived from HepG2 cell lines that are incubated with a bile salt precursor compound and test agent to measure a test agents effect on bile salt export transport and/formation.

This method is readily adaptable to a variety of high throughput screening approaches where hepatocyte preparations or stable cell lines can be used in incubations with bile salt precursor compounds and test agents and post-incubation measurements of bile salt extracellular and/or intracellular concentrations are determined.

An advantage of the present subject matter is the ability to assess test agents ability to inhibit, induce, activate, and/or regulate bile salt export transport and/or formation without using radioactive materials. Furthermore, the method can be adapted to a variety of incubation preparations including hepatocyte suspension and plating as well as stable cell line such as HepG2 suspensions or plating. The method is not limited to any specific incubation formats such as the size and number of incubation chambers.

Furthermore, the present subject matter can be provided in the form of kit comprising buffers, reagents, chemicals, bile salt precursor compounds, bile salts, internal standard, incubation platforms, and directions that allows a person skilled in the art to practice the present invention.

Even furthermore, the method allows for the ability to assess metabolites derived from test agents for their potential to inhibit, induce, activate, and/or regulate bile salt export transport and/or formation.

Finally, the presently disclosed method and kit can be used to identify chemicals or biologics which have potential to cause liver injury, drug-drug, interactions, and/or could be used as therapeutic agents for the treatment of cholestasis, abnormality of bile salt metabolism, liver diseases and cholesterol abnormality.

DETAILED DESCRIPTION OF THE INVENTION

Figure 1:
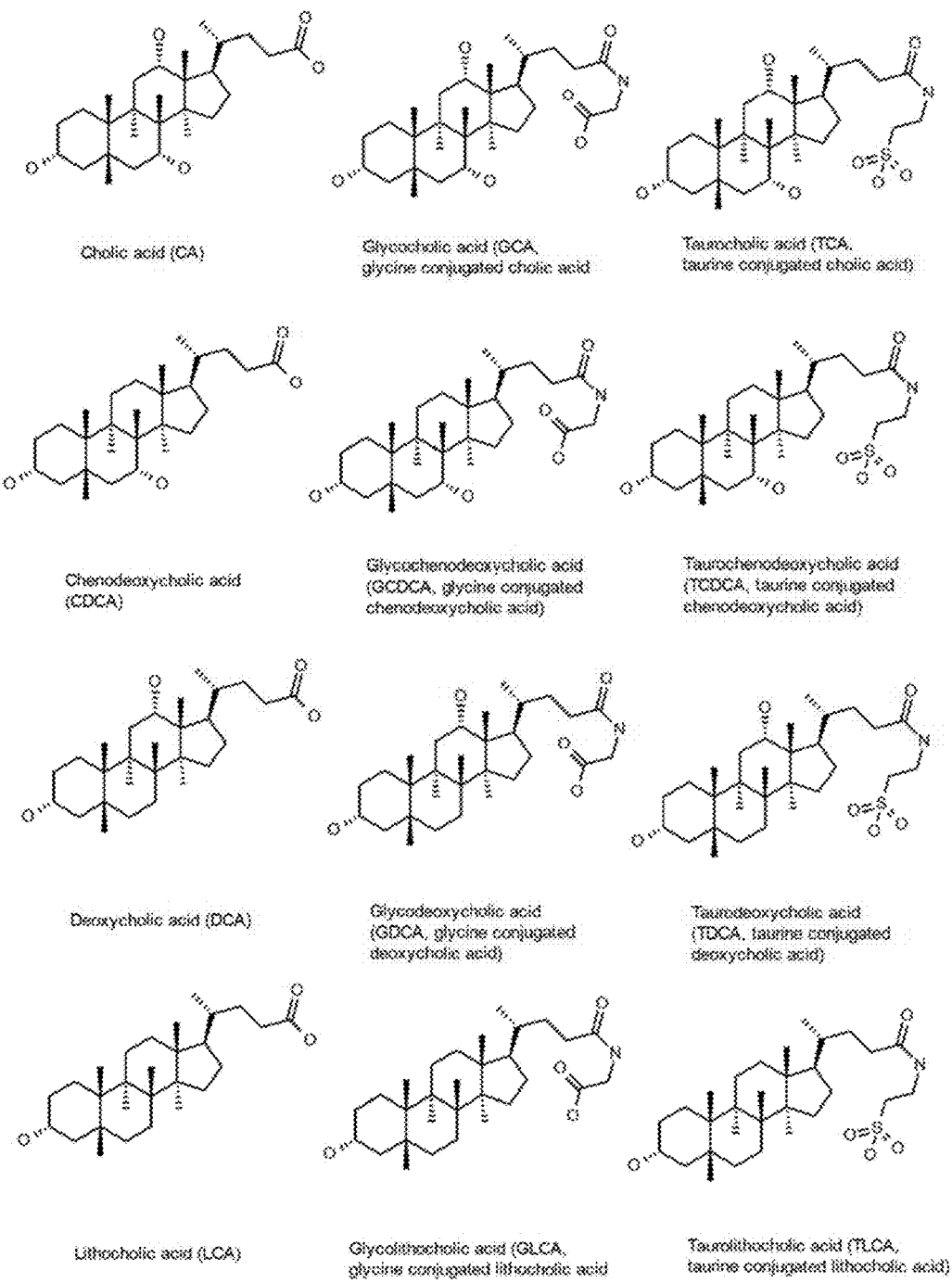
FIG. 1: Chemical structures of bile acids (bile salt precursor compounds) and bile salts (conjugate bile acids).
Figure 2:
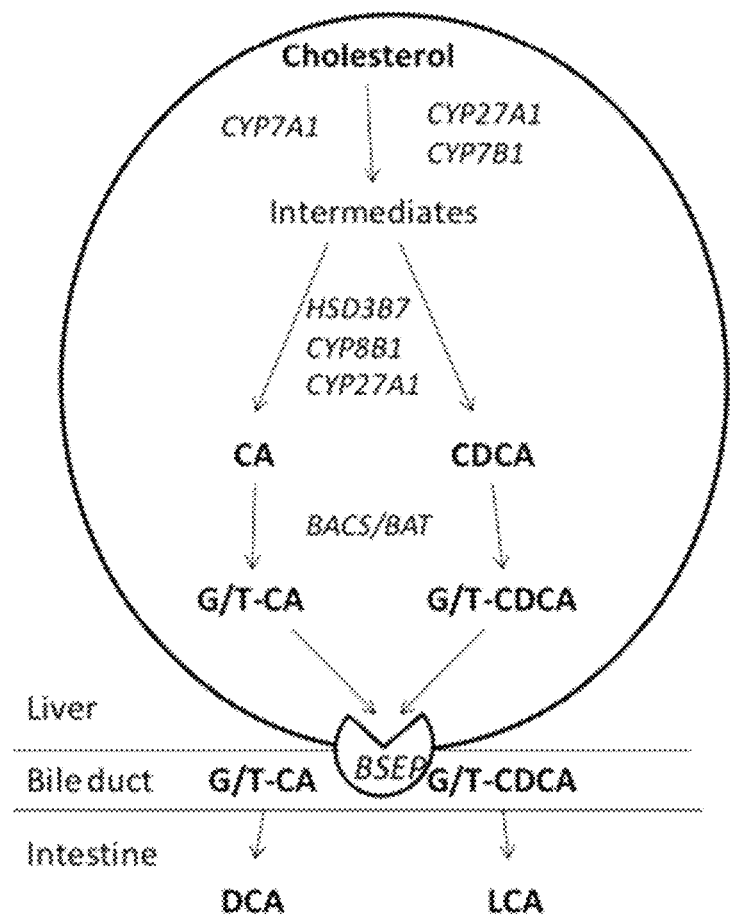
FIG. 2: Bile acid metabolic pathway starting from cholesterol metabolism in the liver hepatocyte whereby cholesterol undergoes oxidative metabolism either by the cytochrome P450 CYP7A1 cytochromes P450 CYP27A1/BYP7B1 to intermediates. The intermediates are further oxidatively metabolized to cholic acid and chenodeoxycholic acid, respectively, and conjugated with the amino acids glycine (G) or taurine (T) to form conjugated bile acids or bile salts that are excreted from the hepatocyte into the bile duct by the membrane transporter protein Bile Salt Export Pump (BSEP). From the bile duct, the formed bile salts are secreted into the intestine.

In relation to the presently disclosed subject matter, a novel method is provided for measuring a test agent's ability to modulate bile salt export transport and/or formation activity in preparations of human and animal hepatocytes or in stable hepatic derived cell lines such as HepG2 by incubation of a bile salt precursor compound or compounds and the said test agent in said preparations followed by measuring extracellular and intracellular bile salt concentrations post-incubation. The test agents used in the present invention include but are not limited to drugs, drug candidates, biologicals, food components, herb or plant components, proteins, peptides, oligonucleotides, DNA and RNA. Interference with bile salt export transport and/or formation is associated with drug-drug interactions and drug-induced liver injury. The bile salt export transport and/or formation activity modulation includes but is not limited to inhibition, induction, activation and/or regulation. Furthermore, the method allows liar a test agent-derived metabolite(s) to be tested for modulation of bile salt export transport and/or formation activity. The present invention can be provided in the form of kit comprising buffers, reagents, chemicals, bile salt precursor compounds, bile salts, internal standard, incubation platforms, paper and/or electronic directions and additional materials necessary to allow a person skilled in the art to practice the present invention.

Furthermore, the presently disclosed invention to measure a test agent's ability to modulate bile salt export transport and/or formation can be used by a person skilled in the art as a drug discovery screen for testing said agent's potential to cause liver injury, drug-drug interactions, and/or potential as a therapeutic for purposes of treating a condition such as cholestasis, abnormality of bile salt metabolism, liver diseases and cholesterol abnormality. Even further, the present invention can be used as part of a drug discovery-screening paradigm.

Hepatocytes have specific membrane domains, that one skilled in the art would recognize including but not limited to an apical (canalicular) membrane or domain and a basolateral (blood or sinusoidal domain) membrane or domain. The hepatocyte basolateral membrane or domain is involved in the uptake into the cell of drugs and xenobiotics, while the apical membrane or domain provides a route for intracellular produced bile salts to be excreted or transported out of the cell into the bile flow. [Morgan et al., id. page 485] Transport of bile salts out of hepatocytes into bile primarily involves transporter proteins located on the cells apical membrane. [Morgan et al., id.]

ATP-binding cassette (ABC) transporters constitute one of largest families of membrane transport proteins and can transport a wide range of different substrates ranting from small ions to large proteins across biological membranes using ATP as an energy source. [Ellinger et al., Detergent screening and purification of the human liver ABC transporters BSEP (ABCB11) and MDR3 (ABCB4) expressed in the yeast *Pichia pastoris*, PLOS One 8(4), 1-12, 2013, page 1] In hepatocytes, eleven ABC transporters are expressed including three ABC transporters involved in bile formation—BSEP (ABCB11), MDR3 (ABCB4) and ABCG5/8. [Ellinger et al., id. page 1]

One of the transporters in the apical or canalicular domain of hepatocytes is the transporter protein named bile salt export pump. [Morgan et al. id. page 485] Bile salt export pump is abbreviated as BSEP in the case of the human protein and Bsep in the case of the animal protein while the corresponding gene for the human protein is labeled BSEP and the animal Bsep. BSEP was formerly known as sister of permeability-glycoprotein or s-PGP based on its close amino acid sequence similarity to P-glycoprotein. [Kis et al., id. page 1878] BSEP is responsible for the elimination of monovalent conjugated bile salts into the bile canaliculi. The bile salt export pump is the main bile salt transporter in human hepatocytes. [Ellinger et al., id. page 1]

Interference in BSEP function can lead to impaired hepatobiliary secretion of bile salts producing an increase in serum and tissue levels of bile salts that can result in cellular mitochondrial damage, apoptosis (programmed cell death) and necrosis. [de Buy Wenniger et al., id.] Genetic defects or mutations in BSEP that interfere with hepatobiliary secretion of bile salts are associated with at least three clinical forms of liver disease: (1) progressive familial intrahepatic cholestasis type 2 (PFIC2); (2) benign recurrent intrahepatic cholestasis type 2 (BRIC2); and (3) intrahepatic cholestasis of pregnancy. [Morgan et al., id. page 486] In the case of PFIC2, the condition has been associated with one or more polymorphisms in the genetic code for BSEP leading to inadequate BSEP function and associated liver injury. PFIC2 is characterized by progressive liver damage usually requiring transplantation while BRIC2 is characterized by intermittent and non-progressive cholestasis.

BSEP protein levels have been correlated with taurocholate transport activity in in vitro studies showing that patients with PFIC2 and BRIC2 gene mutations correlate with decreased protein expression. [Byrne et al., id.] Studies indicate that the extent of the decrease in BSEP expression and function corresponds to disease outcome. [Morgan et al., id. page 486; Kagawa et al 2008]

In the presently disclosed subject matter, bile salt export transport is used as a marker for BSEP and/or any additional bile salt transporters involved in the excretion from hepatocytes of bile salts.

Therapeutic agents that interfere with BSEP function have also been associated with liver injury and cholestasis in humans. [Morgan et al., id. page 486] Examples of drugs implicated include bosentan (an endothelin antagonist for pulmonary arterial hypertension [PAH]), erythromycin estolate (a macrolide antibiotic), nefazodone (5-$HT_2$ receptor antagonist for depression), CI-1034 (an experimental endothelin antagonist for pulmonary arterial hypertension [PAH]), and CP-724, 714 (an experimental HER2 kinase inhibitor for oncology). [Morgan et al., id. page 486]

The potential for drugs that inhibit BSEP function to lead to drug-drug interactions was investigated using a rat sandwich-culture model of bile salt export elimination. [Jemnitz et al., id.] In this study, the 3-hydroxy-3-methylglutauryl coenzyme A reductase inhibitor rosuvastatin, which is eliminated primarily unchanged by transporters, was used as a marker of transporter elimination. Various known inhibitors of elimination transporters were tested for effect on rosuvastatin elimination including the BSEP inhibitors cyclosporine A, glibenclamide and troglitazone. Results showed that cyclosporine A, glibenclamide and troglitazone interfered 32.6%, 29.3% and 20.6%, respectively, with rosuvastatin elimination. The investigators concluded that a potential exists for drug-drug interactions with test agents that interfere with BSEP function.

In modern drug discovery and development, assessing the potential for a drug candidate to produce clinical drug-induced liver injury (DILI) and drug-drug interactions is a major issue. Several drugs have reached marketing approval in the United States by the Food and Drug Administration and have later been found to produce unexpected DILI. The extremely low rate of DILI, in some cases at rates estimated to be about 1 in 10,000, have limited the utility of clinical trials, with patient populations in hundreds to low thousands, to predict this adverse reaction. Preclinical animal models and toxicity studies often don't show any evidence of DILI. Therefore, drug discovery and development scientists have tried to develop in vitro models to predict a potential for DILI. Most of these methods focus on formation of reactive metabolites, drug effects on hepatic mitochondrial function and potential for drug-induced apoptosis (programmed cell deaths). These methods are highly complex and difficult to interpret, which limits their utility as a drug discovery screening approach.

More recently, a greater appreciation has been realized for DILI being the result of interference with bile salt elimination. As mentioned above, it has now been found that several drugs known to cause DILI have been found to interfere with bile salt transport out of hepatocytes. DILI toxicities include cellular mitochondrial damage, apoptosis (programmed cell death) and necrosis. The result of the toxicity can be cholestasis, a condition where bile cannot flow from the liver to the duodenum. The ultimate result of DILI can be the need for liver transplantation.

The need for model systems and methods to assess the ability of drugs and test agents to interfere with bile salt export transporters has led to the development of several in vitro approaches including: (1) sandwich-culture hepatocytes (SCH); (2) BSEP transfected Sf9 insect cell membrane vesicle models; (3) canalicular membrane vesicles (CMV) derived from rat and human whole liver; and (4) doubly-transfected with BSEP and sodium taurocholate co-transporting polypeptide (NTCP). As describe above, each of these methods suffers from issues including reliability, difficulty in preparation of test systems, ability to incorporate in drug discovery paradigms, false positives and negatives, and extrapolation to human hepatic function.

Therefore, there exists a need to develop a method that can be used by one skilled in the art to accurately and reliably measure a test agent's ability to modulate bile salt export transport and/or formation. Furthermore, the method should be flexible to allow for studies of a variety of test agents and should offer the potential to assess the ability of test agent-derived metabolites to modulate bile salt export transport and/or formation. Even furthermore, the method should be readily adaptable for several different hepatocyte incubation preparations including human and animal. The method should offer the potential to be used with stable cell lines such as HepG2. The method should minimize or not require the use of radiolabeled chemicals to measure bile salt transport and/or formation. Even further, the method should be adaptable to drug discovery screens and utilize incubation platforms that allow a test agent to be screened at appropriate concentrations and incubation periods.

The present disclosed subject matter provides for a method to measure modulation of transport and formation of bile salts produced in hepatocyte preparations comprising incubation of a bile salt precursor compound with or without a test agent in said hepatocyte preparations Post incubation concentrations of formed bile salts present in extracellular and intracellular media are measured and used to assess test agent modulation of bile salt export transport and/or formation activity.

Test agents include but are not limited to drug, drug candidate, food component, herb or plant component, amino acid, peptide, protein, oligonucleotide, DNA and RNA. A person skilled in the art would realize that the test agent could be added to the incubation medium in an appropriate solvent or buffer.

Bile acid precursor compounds used in the method include bin are not limited to cholic acid, chenodeoxycholic acid, deoxycholic acid and lithocholic acid individually or in combinations. The bile salt precursor compound is non-radiolabeled in most cases; however, radiolabeled or stable isotope labeled bile salt precursor compounds could be used in the incubation.

Bile salts or conjugated bile acids measured following incubations include but are not limited to glycocholic acid, taurocholic acid, glycodeoxycholic acid, taurodeoxycholic acid, glycolithocholic acid, taurolithocholic acid, glycochenodeoxycholic acid and taurochenodeoxycholic acid.

The bile salt export transport and/or formation activity can be inhibition, induction, activation, or regulation. Inhibition refers to a decrease in bile salt transport and/or formation and can be competitive, non-competitive, uncompetitive or irreversible. Induction refers to an increase in hepatic proteins responsible for bile salt transport or formation of bile salts. Activation refers to the process whereby the test agent would increase the functional activity of the proteins involved in transport and/or formation. Regulation refers to controlling the rates of bile salt transport and/or formation.

Incubations can be conducted using freshly prepared hepatocytes or cryopreserved hepatocytes obtained by standard methods from human and animal livers that one skilled in the art would be well aware of and able to use. The hepatocytes can be used in the form of suspensions or plated on a suitable culture plate containing appropriate growth medium.

In place of hepatocytes, a person skilled in the art could use a stable cell line such as HepG2. HepG2 is a perpetual cell line derived from the liver of a 15-year-old Caucasian male with a well-differentiated hepatocellular carcinoma. Because of the high degree of morphological and functional differentiation in vitro, HepG2 cells can be a suitable model to study the intracellular trafficking and dynamics of bile canalicular and sinusoidal membrane proteins and lipids in human hepatocytes in vitro. [Ihrke et al., WIF-B cells: an in vitro model for studies of hepatocyte polarity. Journal of Cell Biology 123 (6), 1761-1775, 1993]

Presently disclosed is a novel method and embodiments for measuring the modulation of bile salt export transport and/or formation activity by a test agent whereby incubations of hepatocytes from mouse, rat, dog, monkey and human are carried out at concentrations ranging from about 0.001 to about 1.0 million cells/mL and can be conducted in 96-well plates with about 0 μM to about 1000 μM cholic acid or chenodeoxycholic acid in William E buffer in the presence or absence of test agents at concentrations ranging from about 0 μM to about 1000 μM at 37° C. under 5% $CO_2$ for 0 to 4 hours. After incubation, the 96-well plate is centrifuged at 2000 RPM for 15 minutes at room temperature. The supernatant is removed from the cell pellet and labeled as extracellular media.

The hepatocyte cell pellet is re-suspended in William E buffer and subjected to a standard freeze-thaw procedure and sonication to lyse cell membranes. Separately, the 2000 RPM supernatant (extracellular media) and the cell lysate (intracellular media) are mixed with 3 times the volume acetonitrile, and the resultant mixtures are centrifuged at 4000 RPM for 20 minutes at 4° C. An internal standard suitable for liquid chromatography-mass spectrometry measurements of bile salts, such as carbutamide, is added to the acetonitrile diluted supernatants.

Measurement of bile salts in the extracellular media and/or intracellular media can be accomplished by using standard liquid chromatography-mass spectrometry with multiple reaction monitoring of specific ions associated with glycocholic acid (GCA), glycochenodeoxycholic acid (GDCA), taurocholic acid (TCA) and/or taurochenodeoxycholic acid (TCDCA). Quantitation of bile salts in intracellular and extracellular media is performed using standard curves prepared from reference bile salts.

Following quantitation of selected bile salts in the extracellular and intracellular media, calculations are made for bile salt export transport and/or formation activity. In the case of bile salt export transport activity, the concentration of the measured bile salt in the extracellular media is divided by the hepatocyte cell concentration and the length of incubation. This relates to the amount of bile salt exported into the extracellular media during the course of incubation. The selection of bile salt to measure is based on the bile salt precursor compound used in the incubation.

Bile salt formation activity is calculated by first determining the total bile salts formed in the incubation. This is determined by adding the amount of bile salts in the extracellular media with the amount in the intracellular media. The total bile salt amount is than divided by the hepatocyte cell concentration and the length of incubation.

The effect of a test agent in terms of percentage (%) inhibition on bile salt export transport and/or formation activity is determined by the following equation:

$$\% \text{ Inhibition} = \frac{\left(\frac{\text{Activity without Test Agent} -}{\text{activity with test agent}}\right) \times 100}{(\text{Activity without Test Agent})}$$

In one embodiment of the disclosed subject matter, incubations of hepatocytes from mouse, rat, dog, monkey and human are carried out at concentrations ranging from about 0.001 to about 0.25 million cells/mL and can be conducted in 96-well plates with about 0 µM to about 1000 µM cholic acid or chenodeoxycholic acid in William E buffer in the presence or absence of test agents at concentrations ranging from about 0.01 µM to about 1000 µM at 37° C. under 5% $CO_2$ for about 0 to 4 hours.

In yet another embodiment of the disclosed subject matter, incubations of hepatocytes from mouse, rat, dog, monkey and human at concentrations ranging from about 0.001 to about 0.25 million cells/mL can be conducted in 96-well plates with about 0 µM to about 100 µM cholic acid or chenodeoxycholic acid in William E buffer in the presence or absence of test agents at concentrations ranging from about 0.01 µM to about 1000 µM at 37° C. under 5% $CO_2$ for about 1 hour.

In even yet another embodiment of the disclosed subject matter, incubations of hepatocytes derived from human and animal liver at concentrations ranging from about 0.001 to about 0.25 million cells/mL can be conducted in 96-well plates with about 10 µM cholic acid or chenodeoxycholic acid in William E buffer in the presence or absence of test agents at concentrations ranging from about 0.01 µM to about 1000 µM at 37° C. under 5% $CO_2$ for about 1 hour.

In another embodiment of the method, one skilled in the art would appreciate, that the investigator can practice the method with hepatocytes prepared from human and animal livers derived from warm-blooded mammals including mouse, rat, dog, rabbit, and monkey. Hepatocytes can be prepared from individual livers or as a pooled sample of hepatocytes derived from multiple different human or animal livers.

In another embodiment, a person skilled in the art would recognize that the method is not limited to 96-well plates but can readily be modified for use with a variety of incubation platforms including a petri dish with cells plated in a monolayer, a single or multi-well plate formats.

In yet another embodiment, one skilled in the art would readily recognize that bile salts formed in the present method can be separated from the extracellular and intracellular media by a variety of techniques including but not limited to solid phase extraction with C18, C8, or anion exchange solid support, or by liquid liquid extraction, or addition of acetonitrile, methanol, or any suitable solvent followed by centrifugation or filtration.

A person skilled in the art would recognize that additional methods for quantitation of bile salts are available to the investigator that include but are not limited to HPLC, mass spectrometry, radioactivity counting, enzyme assay, and/or fluorescence.

An additional embodiment of the presently disclosed method can be practiced to investigate a test agent's effect on ADME related processes. As skilled in the art would readily recognize, the method can be used to allow for the measurement of test agent-derived metabolites to inhibit, induce, activate, and/or regulate bile salt export transport and/or formation. In yet another embodiment of the method, it can be modified whereby selective drug metabolizing enzyme inhibitors can be co-incubated with test agents to measure effect on bile salt export transport and/or formation. In another embodiment, one skilled in the art would appreciate, the method can be practiced to allow for measurement of interactions between a test agent and known modulators of bile salt export transport and/or formation.

In another embodiment, the method can be used with human and/or animal hepatocytes that have ADME enzyme phenotypes that can allow for measuring the effect of specific hepatic phenotype on a test agent's modulation of bile salt export transport and/or formation. For example, hepatocytes derived from a human liver expressing a genetic polymorphism deficiency in cytochrome P450 2D6 enzyme activity can be used in the method to measure a test agent's modulation on bile salt export transport and/or formation.

As one skilled in the art would appreciate, the present method can be used as a drug discovery-screening assay to measure multiple test agents' effect on bile salt export transport and formation activity. The assays can include known inhibitors and non-inhibitors of bile salt export transport. Results from the screening assay can be used for selection or ranking of test agents modulation of bile salt export transport and/or formation. Furthermore, the method can be practiced to determine in vitro $IC_{50}$ values for test agents. Additionally, the results can be used as part of an in vitro-in vivo correlation of bile salt export transport activity profile.

The presently disclosed subject matter for the method to measure a test agent's modulation of bile salt export transport and/or formation activity and embodiments can be practiced to identify chemicals or biological test agents which have potential to cause liver injury, drug-drug interactions, and/or can be used as therapeutic agents for the treatment of cholestasis, abnormality of bile salt metabolism, liver diseases and cholesterol abnormality.

The presently disclosed subject matter and embodiments can be provided in the form of kits comprising hullers, reagents, chemicals, bile salt precursor compounds, bile salts, internal standard, incubation platforms, and directions that allows a person skilled in the art to practice the instant disclosure.

The references cited in the specification are incorporated herein by reference to the extent that they supplement, explain, provide a background for or teach methodology, techniques and/or compositions employed herein. The following examples have been included to illustrate representative modes of the invention. In light of the present disclosure, one of ordinary skill in the art will appreciate that the following examples are intended to be representative only and that numerous changes, modifications and alterations can be employed without departing from the spirit of the invention.

Abbreviations: ADME; absorption, distribution, metabolism and excretion; BRIC2; benign recurrent intrahepatic cholestasis type 2; BSEP: bile salt export pump; CMV: canalicular membrane vesicles; CA: cholic acid; CD: chenodeoxycholic acid; DCA: deoxycholic acid; DILI: drug induced liver injury; DNA: deoxyribonucleic acid; GCA: glycocholic acid or glycocholate; GDCA: glycodeoxycholic acid or glycodeoxycholate: GCDCA: glycochenodeoxycholic acid or glycochenodeoxycholate; GLCA: glycolithocholic acid or glycolithocholate; HPLC: high performance liquid chromatography; LC/MS/MS: liquid chromatography coupled with a tandem mass spectrometry; LA: lithocholic acid; MDR1: multidrug resistance protein 1; MRM: multiple ion monitoring; PFIC2; progressive familial intrahepatic cholestasis type 2; RNA: ribonucleic acid; SCH: sandwich-culture hepatocytes; s-Pgp: sister P-glycoprotein; NTCP: sodium taurocholate co-transporting polypeptide; Sf9: *Spodoptera frugiperda* ovarian cells; TCA: taurocholic acid; TCDCA: taurochenodeoxycholic acid; TDCA: taurodeoxycholic acid; TLCA: taurolithocholic acid.

EXAMPLES

The following examples have been included to illustrate the representative modes of the invention. One of ordinary skill in the art will appreciate that the following examples are intended to be representative only and that additional variations and modifications can be employed without departing from the spirit and scope of the presently disclosed subject matter.

Experimental Procedures

Unless specifically stated otherwise, the following experimental procedures were applied.

Chemicals and Biochemicals: Cholic acid, chenodeoxycholic acid, deoxycholic acid, lithocholic acid, glycocholate, taurocholate, glycodeoxycholate, taurodeoxycholate, glycolithocholate, taurolithocholate, glycochenodeoxycholate and taurochenodeoxycholate were purchased from Sigma-Aldrich (St Louis, Mo., USA). Mouse, rat, dog, monkey and human hepatocytes and In VitroGRO HT medium were obtained from Celsis IVT, Williams Medium E was purchased from GIBCO. Other reagents were purchased from Sigma-Aldrich unless stated otherwise in the text.

Preparation of hepatocytes: Functional hepatocytes to be employed in any variation of the present bile salt export transport and/or formation activity assay can, as one skilled in the art would be well aware of, be derived from cryopreserved hepatocytes (stored at about −78° C.) or freshly prepared from liver and may be co-cultured with other cell types such as stromal cells and Kuffer cells. Hepatocytes should have high cell viability (>80%), high activity to form bile salts and metabolites (>0.1 nmole/million cells/hr) and high activity (>0.1 nmole/million cells/hr) to transport bile salts and other substances.

Fifty ml In VitroGRO HT Medium was pre-warmed in a 37° C. water bath. A vial of hepatocyte was removed from a liquid $N_2$ tank and quickly warmed up in a 37° C. water bath by holding in hand with slow rotation. As soon as the edge of the frozen cells was separated from the wall of the vial, the frozen cells were poured into the pre-warmed HT medium, the remaining cells in the vial were collected using pipette. The tube was centrifuged at 50 g, 25° C. for 5 minutes, the supernatant was removed and the cell pellet was re-suspended in 8 ml of pre-warmed William E buffer, the cell numbers were counted in a hemocytometer. The yield was $1 \times 10^6$ cells/ml. The cells were counted in 0.4% Trypan blue (80 µl William E+10 µl Trypan blue stock+10 µl cells). The hepatocyte concentration was adjusted with William E buffer to meet the objectives of various experiments.

LC/MS/MS assays: Liquid chromatography was carried out using a Shimadzu (Columbia, Md.) HPLC system consisting of a SCL-10Avp system controller, two LC-10ADvp pumps, a CTC HTC PAL autosampler, a Shimadzu SPD-10ADvp UV detector and an automated switching valve. The switching valve was used to divert the column effluent to either waste or to the MS instrument. The Shimadzu HPLC system was used for sample injection and analyte separation. Each sample was loaded onto a reverse phase column, Waters (Milford, Mass.) Symmetry Shield RP8 5u 2.1 mm×50 mm. The column chamber's temperature was ambient. The initial HPLC mobile phase conditions used for separation and elution of analytes comprised 2 mM ammonium acetate buffer in water containing 0.1% formic acid and 10% acetonitrile. The flow rate was 0.5 mL/min. The amount of acetonitrile in the mobile phase was ramped linearly up to 40% over a 2-minute period followed by a rapid increase to 95% acetonitrile in 0.5 minutes. After holding at 95% acetonitrile for 1.2 minutes, the mobile phase was reset to the initial conditions in 0.1 minute. The analytical column was equilibrated with the starting mobile phase for 1.2 minutes. The total run time for each sample analysis was approximately 5 minutes.

The HPLC elute was injected into an AB Sciex API3000 LC/MS/MS system (Framingham, Mass.) equipped with a Turbo IonSpray source set with a desolvation temperature of 450° C. Nitrogen was used as curtain gas, nebulizer gas, heater gas and collision gas. Data for bile acids and salts was acquired in the positive ion mode using multiple reaction monitoring methods (MRM). The ion transitions of the MRM method for specific detection of GCA, TCA, GDCA, TDCA, GLCA, TLCA, GCDCA and TCDCA were developed in standard fashion. Carbutamide was used as internal standard (IS), m/z 272/156. Ionspray voltage was set at 4000 V and the collision gas (CAD) set at 6. Declustering potential was set at 82, 46 and 49 for GCA, TAC, and IS, respectively. Collision energy was set at 25, 33, and 23 eV for GCA, TAC, and IS.

Data analysis: Extracellular concentrations of bile salts were determined by LC/MS/MS MRM analysis of the 2000 RPM supernatant fractions post-incubation. Intracellular concentrations of bile salts were determined by LC/MS/MS MRM of hepatocyte cell lysate obtained after rupturing of cell membranes post incubation. Bile salt export transport and/or formation activity and test agent percent inhibition were calculated using the following equations:

$$\text{Bile Salt Export Transport Activity} = \frac{(\text{Extracellular Conc. Bile Salts})}{(\text{Hepatocyte Conc.}) \times (\text{Incubation Time})}$$

$$\text{Total Bile Salts} = \text{Amount Extracellular} + \text{Amount Intracellular}$$

$$\text{Bile Salt Formation Activity} = \frac{(\text{Total Bile Salts})}{(\text{Hepatocyte Concentration}) \times (\text{Incubation Time})}$$

$$\% \text{ Inhibition} = \frac{\left(\frac{\text{Activity without Test Agent} - }{\text{Activity with Test Agent}}\right) \times 100}{(\text{Activity without Test Agent})}$$

Kinetic parameters were calculated using standard Michaelis-Menten kinetics. $IC_{50}$ values were determined using Prism software (La Jolla, Calif.) or median-effect equation. [Chou et al., Theoretical basis, experimental design, and computerized simulation of synergism and antagonism in Drug Combination Studies. Pharmacological Reviews 58, 621, 2006]

Example 1

Effects of hepatocyte density on the transport and formation of bile salts: Hepatocytes were prepared in suspension in William E buffer at concentrations ranging from 0 to 1 million cells/mL. After pre-incubation in a 96-well plate for 10 minutes at 37° C. under 5% $CO_2$, the hepatocyte suspensions were incubated with cholic acid or chenodeoxycholic acid at 100 μM in the final volute of 100 μL at 37° C. under 5% $CO_2$ for 1 hour. Experiments were carried out in triplicate or duplicate. Suspensions were then centrifuged at 2000 for 15 minutes at room temperature. The hepatocyte cell pellets were re-suspended in William E buffer and subjected to a standard freeze-thaw procedure and sonication to lyse cell membranes. Separately, the 2000 RPM supernatants and the cell lysates were mixed with 3× volume acetonitrile, and the mixtures centrifuged at 4000 RPM for 20 minutes at 4° C. The supernatants were analyzed by LC/MS/MS for glycocholate, glycochenodeoxycholate, taurocholate and or taurochenodeoxycholate.

Figure 3:
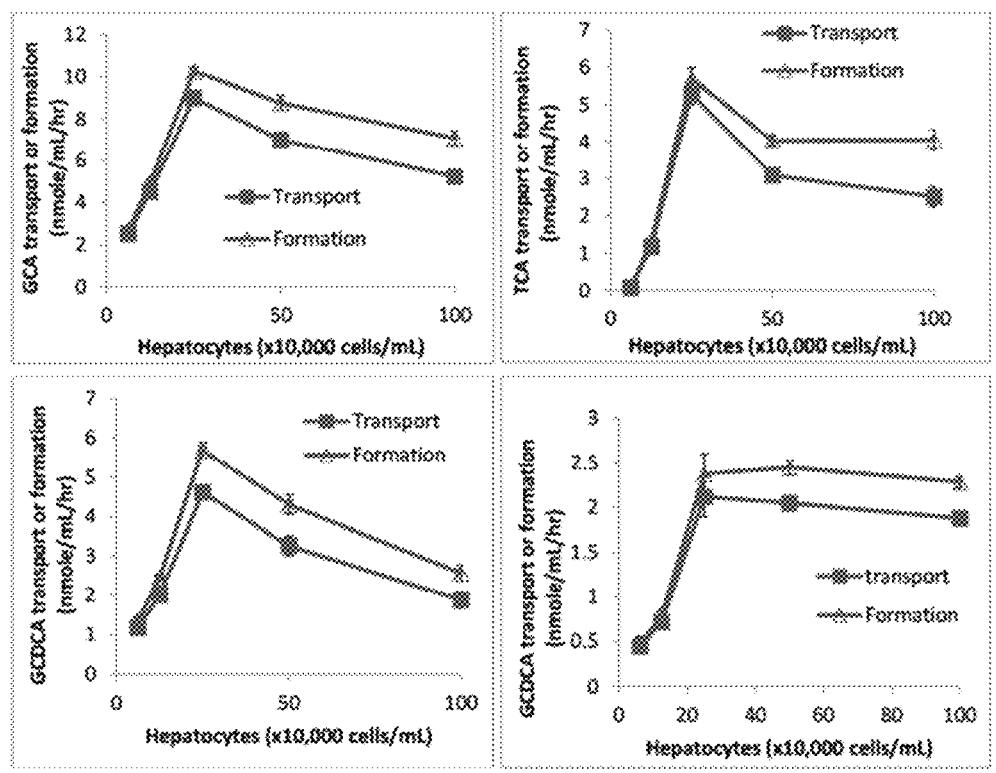
FIG. 3: Effect of hepatocyte concentration or density on the transport and formation of bile salts in human hepatocytes. Upper panel: human hepatocytes (0.25 million cells/mL) were incubated with cholic acid (CA, 100 µM) for 1 hour and the transport and formation of glycocholate (GCA, left) or taurocholate (TCA, right) determined; lower panel: human hepatocytes (0.25 million cells/mL) were incubated with chenodeoxycholic acid (CDCA, 100 µM) and the transport and formation of glycochenodeoxycholate (GCDCA, left) and taurochenodeoxycholate (TCDCA, right) determined.

The transport and formation of bile salts increased with hepatocyte concentration starting from 0 cells/mL and increasing to 0.25 million cells/mL. At hepatocyte concentrations above 0.25 million cells/mL, transport and formation values reached a plateau or decreased (FIG. 3). The transport and formation of bile salts were closely correlated with each other.

Example 2

Time courses for transport and formation of bile salts in hepatocytes: Hepatocytes at 0.25 million cells/ml were incubated with cholic acid or chenodeoxycholic acid in William E buffer at 100 μM in the final volume of 100 μL at 37° C. under 5% $CO_2$ fur various time ranging from 0-4 hours. The suspensions were then centrifuged at 2000 RPM for 15 minutes at room temperature. The hepatocyte cell pellets were re-suspended in William E buffer and subjected to a standard freeze-thaw process and sonication to lyse cell membranes. Separately, the 2000 RPM supernatants and the cell lysates were mixed with 3× volume of acetonitrile, and the mixtures were centrifuged at 4000 RPM for 20 minutes at 4° C. The supernatants were analyzed by LC/MS/MS for glycocholate, glycochenodeoxycholate, taurocholate and/or taurochenodeoxycholate. LC/MS/MS analysis was conducted in duplicate or triplicate.

Figure 4:
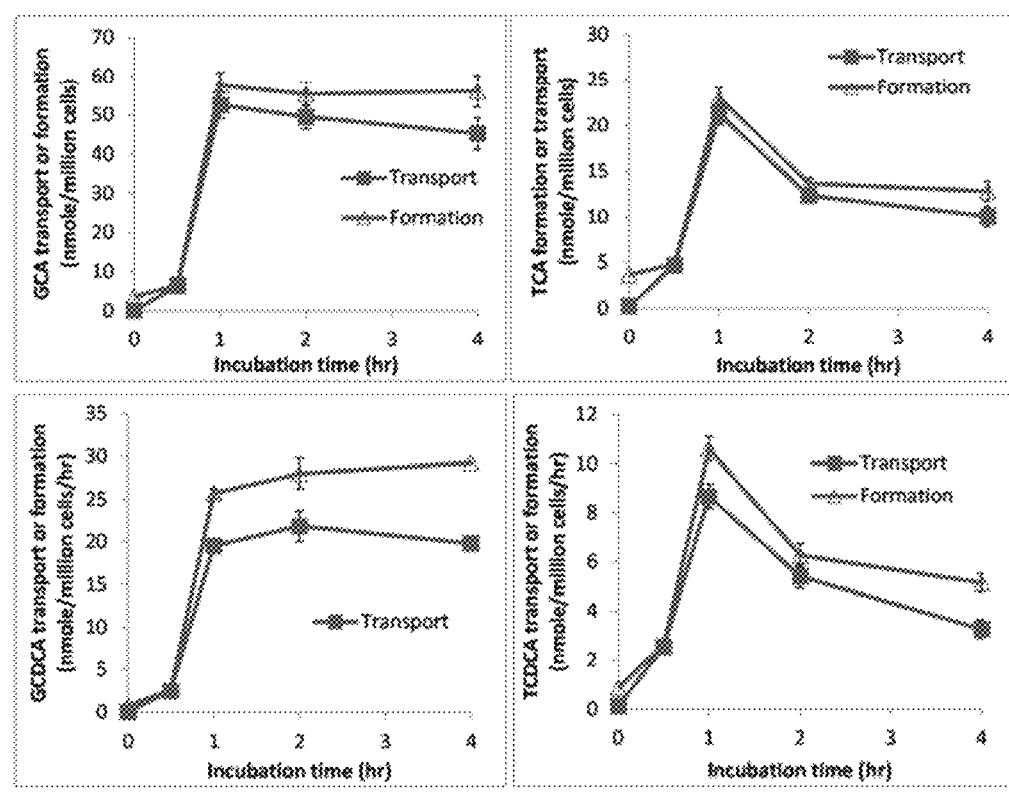
FIG. 4: Effect of incubation time on the transport and formation of bile salts in human hepatocytes. Upper panel: human hepatocytes (0.25 million cells/ml) were incubated with cholic acid (CA, 100 µM) for various times and the transport and formation of glycocholate (GCA, left) or taurocholate (TCA, right) determined; lower panel: human hepatocytes (0.25 million cells/mL) were incubated with chenodeoxycholic acid (CDCA, 100 µM) for various times and the transport and formation of glycochenodeoxycholate (GCDCA, left) and taurochenodeoxycholate (TCDCA, right) determined.

The transport and formation of bile salts was increased when the incubation time increased from 0-1 hour, but reached a plateau or decreased when the incubation time was longer than 1 hour (FIG. 4). The transport and formation of bile salts were closely correlated with each other.

Example 3

Effect of bile acid concentration on the transport and formation of bile salts in hepatocytes: Human hepatocytes at 0.25 million cells/ml were incubated with cholic acid or chenodeoxycholic acid in William E buffer at various concentrations ranging from 0-1000 μL in the final volume of 100 μL at 37° C. under 5% $CO_2$ for 1 hour. The experiments were carried out in duplicate or triplicate. After incubation, the suspensions were centrifuged at 2000-RPM for 15 minutes at room temperature. The cell pellets were re-suspended in William E buffer, and followed by frozen/thaw and sonication to lyse the hepatocytes. Separately, the 2000-RPM supernatants and the cell lysates were mixed with 3× volume of acetonitrile and the mixtures were centrifuged at 4000-RPM for 20 minutes at 4° C. The supernatants were analyzed by LC/MS/MS for glycocholate, glycochenodeoxycholate, taurocholate and/or taurochenodeoxycholate. LC/MS/MS analysis was conducted in duplicate or triplicate.

Figure 5:
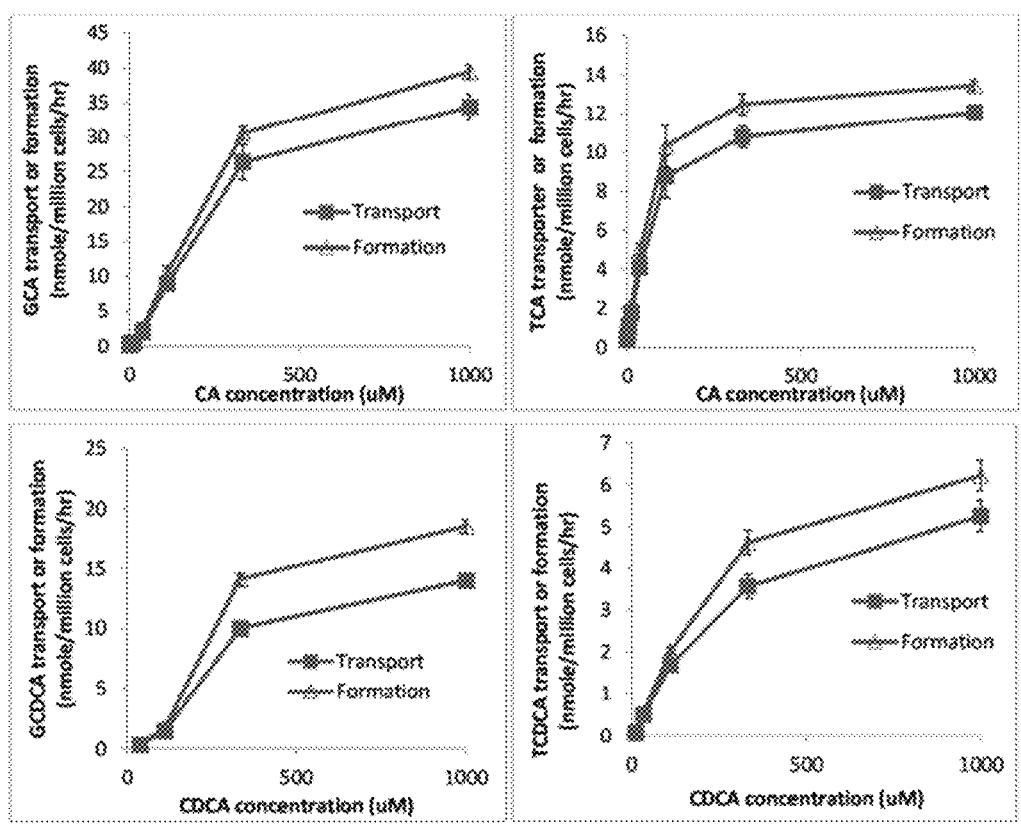
FIG. 5: Effect of cholic acid and chenodeoxycholic acid concentration on the transport and formation of bile salts in human hepatocytes. Upper panel: human hepatocytes (0.25 million cells/ml) were incubated with cholic acid (CA) for 1 hour and the transport and formation of glycocholate (GCA, left) and taurocholate (TCA, right) determined; lower panel: human hepatocytes (0.25 million cells/mL) were incubated with chenodeoxycholic acid (CDCA) for 1 hour and the transport and formation of glycochenodeoxycholate (GCDCA, left) and taurochenodeoxycholic acid (TCDCA, right) determined.

The transport and formation of bile salts were increased when the bile acid concentrations increased, and displayed plateauing or saturation (FIG. 5). The transport and formation of bile salts were closely correlated with each other.

Example 4

Effect of chemicals on the transport and formation of bile salts in hepatocytes: Hepatocytes from mouse, rat, dog, monkey and human at concentrations ranging from 0.1 to 0.25 million cells/mL were incubated in 96-well plates with 10 μM cholic acid or chenodeoxycholic acid in William E buffer in the presence or absence of test chemicals at concentrations ranging from 0.01 to 1000 μM at 37° C. under 5% $CO_2$ for 1 hour. After incubation, the 96-well plate was centrifuged at 2000 RPM for 15 minutes at room temperature. The cell pellets were re-suspended in William E buffer, and followed by frozen/thaw and sonication to lyse the hepatocytes. Separately, the supernatants and the cell lysates were mixed with 3× volume of acetonitrile, and the mixtures were centrifuged at 4000 RPM for 20 minutes at 4° C. The supernatants were analyzed by LC/MS/MS for the glycocholate, glycochenodeoxycholate, taurocholate and taurochenodeoxycholate.

Figure 6A:
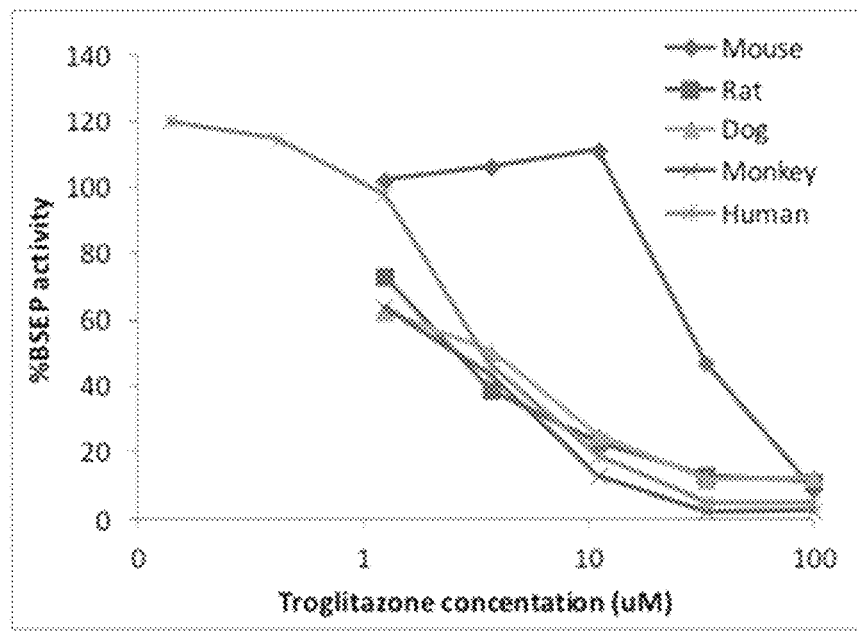
FIG. 6a: The percent inhibition of BSEP (bile salt export transport) activity in mouse, rat, dog, monkey, and human hepatocyte preparations when incubated with various concentrations of the test agent troglitazone, a known inhibitor of BSEP. Incubations were conducted using either 10-µM cholic acid or chenodeoxycholic acid at 37° C. for 1 hour.
Figure 6B:
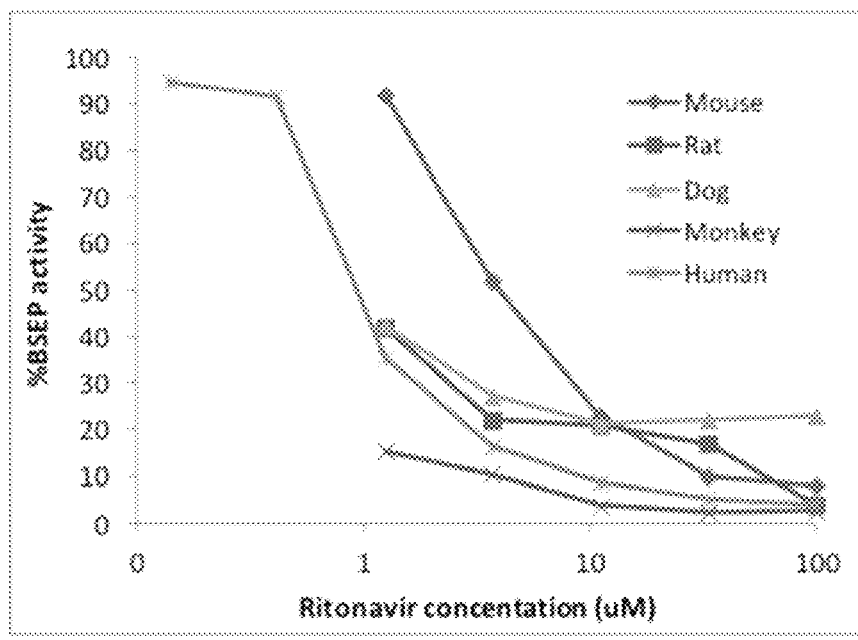
FIG. 6b: The percent inhibition of BSEP (bile salt export transport) activity in mouse, rat, dog, monkey, and human hepatocyte preparations when incubated with various concentrations of the test agent ritonavir, a known inhibitor of BSEP. Incubations were conducted using either 10-µM cholic acid or chenodeoxycholic acid at 37° C. for 1 hour.

Several drugs were tested for the potential modulation of the transport of bile salts in hepatocytes from mouse, rat, dog, monkey and human. Some of the drugs tested are known to cause liver injury and/or cholestasis. The drugs tested include atazanavir, fluconazole, ketoconazole, quinidine, nelfinavir, propranolol, ritonavir, saquinavir, thiotepa, troglitazone, verapamil, vinblastine, crizotinib, quercetin. The results are shown in Tables 1, 2 and 3. The amount of bile salt export transport inhibition is correlated with the incidence of liver injury. Species differences were observed in bile salt export transport inhibition. In general, mouse is less sensitive than other species, and monkey is similar to human in bile salt export transport inhibition. FIG. 6a shows percent inhibition of BSEP activity for the test agent troglitazone while FIG. 6b shows percent inhibition for the test agent ritonavir.

TABLE 1

Inhibition of BSEP activity (transport of glycocholate) by selected drugs in rat, monkey and human hepatocytes.

| | Rat | | Monkey | | Human | |
|---|---|---|---|---|---|---|
| | 1 μM | 10 μM | 1 μM | 10 μM | 1 μM | 10 μM |
| Atazanavir | B** | B | A | B | A | B |
| Fluconazole | A* | A | A | A | A | A |
| Ketoconazole | A | B | A | B | A | A |
| Quinidine | A | A | A | A | A | A |
| Nelfinavir | A | B | A | B | A | B |
| Propranolol | A | A | A | A | A | A |
| Ritonavir | B | B | B | B | B | B |
| Saquinavir | A | B | A | B | A | B |
| Thiotepa | A | A | A | A | A | A |
| Troglitazone | B | B | B | B | B | B |
| Verapamil | A | B | A | A | A | A |
| Vinblastine | A | B | A | A | A | B |
| Crizotinib | A | B | A | A | A | B |
| Quercetin | A | A | A | A | A | A |

*A: <50% inhibition,
**B: >50% inhibition

TABLE 2

Inhibition of BSEP activity (transport of taurocholate) by selected drugs in mouse, dog and monkey hepatocytes.

|  | Mouse | | Dog | | Monkey | |
| --- | --- | --- | --- | --- | --- | --- |
|  | 1 μM | 10 μM | 1 μM | 10 μM | 1 μM | 10 μM |
| Atazanavir | A | A | A | B | A | B |
| Fluconazole | A | A | A | A | A | A |
| Ketoconazole | A | A | A | A | A | B |
| Quinidine | A | A | A | A | A | A |
| Nelfinavir | A | A | A | B | A | B |
| Propranolol | A | A | A | A | A | A |
| Ritonavir | A | B | B | B | B | B |
| Saquinavir | A | A | A | B | A | B |
| Thiotepa | A | A | A | A | A | A |
| Troglitazone | A | A | A | B | A | B |
| Verapamil | A | A | A | A | A | A |
| Vinblastine | A | A | A | A | A | A |
| Crizotinib | A | A | A | B | A | A |
| Quercetin | A | A | A | B | A | A |

*A: <50% inhibition,
**B: >50% inhibition

TABLE 3

IC50 values for inhibition of BSEP activity by selected drugs in hepatocytes from mouse, rat, dog, monkey and human.

|  | Mouse | Rat | Dog | Monkey | Human |
| --- | --- | --- | --- | --- | --- |
| Ritonavir | B** | A* | A | A | A |
| Ketoconazole | C*** | C | B | B |  |
| Rifampicin | C | B | C | A |  |
| Troglitazone | C | B | B | B | B |

*A: IC50 < 1 μM;
**B: 1 uM < IC50 < 10 μM;
***C: IC50 > 10 μM

I claim:

1. A method for assessing a test agent's effect on bile salt export transport and/or formation activity comprising:
   (a) separately incubating a hepatocyte suspension preparation and a bile salt precursor with and without a test agent at about 37° C. under conditions allowing bile salt export transport and/or formation for a time sufficient to assess bile salt export transport and/or formation activity of bile salt precursor derived bile salts,
   (b) post-incubation separating extracellular media and intracellular media of the hepatocyte suspension preparations; and
   (c) quantifying the bile salt precursor derived bile salts present in the extracellular and/or intracellular media of the post-incubation hepatocyte suspension preparations.

2. The method of claim 1 wherein the hepatocyte suspension preparation comprises freshly prepared or cryopreserved hepatocytes.

3. The method of claim 1 wherein the hepatocyte suspension preparation comprises hepatocytes derived from human or animal tissue.

4. The method of claim 3 wherein the hepatocytes are derived from human liver tissue.

5. The model system of claim 3 wherein the hepatocytes are derived from mouse, rat, dog, rabbit or monkey liver tissue.

6. The model system of claim 1 wherein the hepatocyte suspension preparation comprises hepatocytes derived from stable cell lines.

7. The method of claim 1 wherein the hepatocyte suspension preparation is a pooled hepatocyte suspension preparation.

8. The method of claim 1 wherein the bile salt precursor compound comprises individually or in combination cholic acid, chenodeoxycholic acid, deoxycholic acid, lithocholic acid and/or derivatives thereof.

9. The method of claim 8 wherein the bile acid precursor comprises cholic acid.

10. The model system of claim 8 wherein the bile acid precursor comprises chenodeoxycholic acid.

11. The method of claim 1 wherein the bile salt precursor derived bile salts comprise glycocholic acid, taurocholic acid, glycodeoxy cholic acid, taurodeoxycholic acid, glycolithocholic acid, taurolithocholic acid, glycochenodeoxycholic acid and/or taurochenodeoxycholic acid.

12. The method of claim 1 wherein the test agent is a drug, drug candidate, food component, herb or plant component, amino acid, peptide, protein, oligonucleotide, DNA, or RNA.

13. The method of claim 12 wherein the test agent is a drug or drug candidate.

14. A method for assessing potential treatments for hepatic cholestasis, drug-drug interactions and drug-induced liver injury comprising the method of claim 1.

15. A method of generating a report for evaluating the Bile Salts Export Pump (BSEP) inhibition potential of a test agent comprising results of a test agent's effect on bile salt export transport and/or formation activity obtained by:
   (a) separately incubating a hepatocyte suspension preparation and a bile salt precursor with and without a test agent at about 37° C. under conditions allowing bile salt export transport and/or formation for a time sufficient to assess bile salt export transport and/or formation activity of bile salt precursor derived bile salt,
   (b) post-incubation separating extracellular media and intracellular media of the hepatocyte suspension preparations;
   (c) quantifying the bile salt precursor derived bile salts present in the extracellular and/or intracellular media of the post-incubation hepatocyte suspension preparations; and
   (d) reporting the results of a test agent's effect on bile salt export transport and/or activity as percent inhibition, $IC_{50}$, and/or $K_i$.

16. The method of generating a report of claim 15 wherein the test agent is a drug and/or a drug candidate.

17. The method of generating a report of claim 15 further comprising results for at least one reference agent.

* * * * *